United States Patent
Ogura et al.

(10) Patent No.: US 6,784,228 B2
(45) Date of Patent: Aug. 31, 2004

(54) EPOXY RESIN COMPOSITION, CURED ARTICLE THEREOF, NOVEL EPOXY RESIN, NOVEL PHENOL COMPOUND, AND PROCESS FOR PREPARING THE SAME

(75) Inventors: Ichiro Ogura, Ichihara (JP); Yoshiyuki Takahashi, Ichihara (JP); Tomoyuki Imada, Ichihara (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 58 days.

(21) Appl. No.: 10/190,491

(22) Filed: Jul. 9, 2002

(65) Prior Publication Data

US 2003/0092852 A1 May 15, 2003

(30) Foreign Application Priority Data

Jul. 12, 2001 (JP) ..................................... P2001-212069
Oct. 24, 2001 (JP) ..................................... P2001-326305

(51) Int. Cl.$^7$ ............................. C08K 3/36; C08L 63/02
(52) U.S. Cl. ..................... 523/466; 528/98; 549/356; 549/358; 549/543; 549/544; 549/555; 568/717; 568/722; 568/727; 568/728; 568/735
(58) Field of Search ................................. 549/356, 358, 549/543, 544, 555; 568/717, 722, 727, 728, 735; 523/466; 528/98

(56) References Cited

U.S. PATENT DOCUMENTS 4,266,020 A    5/1981  Sakai et al. ................. 430/551
5,780,571 A    7/1998  Ohno et al. .................... 528/97

FOREIGN PATENT DOCUMENTS

| EP | 0 915 118 A1 | 5/1999 |
| JP | 01283280 | * 11/1989 |
| JP | 2000038517 | * 2/2000 |

OTHER PUBLICATIONS

Chem. Abstract of J. Applied Polymer Sci.(1982)27(9), pp3289–3312.*

Patent Abstracts of Japan, vol. 2000, No. 5, Sep. 14, 2000 & JP 2000–038517, Feb. 8, 2000.

* cited by examiner

Primary Examiner—Philip Tucker
Assistant Examiner—D. Aylward
(74) Attorney, Agent, or Firm—Armstrong, Kratz, Quintos, Hanson & Brooks, LLP

(57) ABSTRACT

The present invention relates to an epoxy resin composition a cure article thereof, a novel epoxy resin used therein, a polyhydric phenol compound suited for used as an intermediate thereof, and a process for preparing the same. One of the objects to be achieved by the present invention is to exert the heat resistance, the moisture resistance, the dielectric performances and the flame-resistant effect required of electric or electronic materials such as semiconductor encapsulating materials and varnishes for circuit boards in the epoxy resin composition.

18 Claims, 12 Drawing Sheets

EPOXY RESIN COMPOSITION, CURED ARTICLE THEREOF, NOVEL EPOXY RESIN, NOVEL PHENOL COMPOUND, AND PROCESS FOR PREPARING THE SAME

BACKGROUND OF THE INVENTION

1. Field of the Invention

The present invention relates to an epoxy resin composition, a cured article thereof, a novel epoxy resin used in the same, a polyhydric phenol compound suited for use as an intermediate thereof, and a process for preparing the same.

2. Description of Related Art

Thermosetting resin compositions comprising an epoxy resin and a curing agent have widely been used as electric or electronic materials such as semiconductor encapsulating materials and varnishes for circuit boards.

Recently, in the field of semiconductors, although one-surface sealed type packages such as a ball grid array type semiconductor have widely been used, these arises a large problem such as warp of the package after molding. To solve the problem, a sealing resin having a high glass transition temperature is now required. Also in the field of circuit boards, a material having a high glass transition temperature is strongly desired as a means for enhancing the dimensional stability of a multi-layer laminated board.

To improve the heat resistance of a cured article of an epoxy resin, a crosslinking density of the cured article is generally increased. Therefore, it is necessary to increase the concentration of epoxy groups in the epoxy resin. However, according to such a means, the cured article has a lot of secondary hydroxyl groups derived from epoxy groups, thereby impairing properties required of the semiconductor encapsulating material and varnish for circuit boards, for example, moisture resistance and low constant.

For example, Japanese Patent Application, First publication No. Hei 8-27250 and Japanese Patent Application, First publication No. Hei 9-48839 disclose techniques of using a dicyclopentadiene type epoxy resin as an epoxy resin for semiconductor encapsulating materials having excellent heat resistance of the cured article without impairing required properties such as moisture resistance and low constant.

Although the dicyclopentadiene type epoxy resin disclosed in Japanese Patent Application, First Publication No. Hei 8-27250 or Japanese Patent Application, First Publication No. Hei 9-48839 has excellent performances as a semiconductor encapsulating material, for example, excellent heat resistance, water resistance and dielectric properties of the cured article, the use of an additive-based flame retardant such as halogen-based flame retardant or phosphorus-based flame retardant cannot be avoided when used because the dicyclopentadiene type epoxy resin is easy to burn. On the other hand, the halogen-based flame retardant is a factor capable of generating dioxin, while the phosphorus-based flame retardant has a problem of lowering the hydrolytic resistance, in addition to its toxicity. Therefore, an epoxy resin composition has been desired wherein the flame resistance is imparted to the epoxy resin itself without impairing the required properties described above.

SUMMARY OF THE INVENTION

An object to be achieved by the present invention is to exert the heat resistance, the moisture resistance, the dielectric performances and the flame-resistant effect required of electric or electronic materials such as semiconductor encapsulating materials and varnishes for circuit boards in the epoxy resin composition.

Another object to be achieved by the present invention is to provide a novel epoxy resin having excellent heat resistance, moisture resistance, dielectric performances and flame-resistant effects.

Still another object to be achieved by the present invention is to provide a phenol compound suited for use as an intermediate of the novel epoxy resin.

To achieve the objects described above, the present inventors have intensively researched and have found that the flame resistance is markedly improved, in addition to the heat resistance, the moisture resistance and the dielectric properties, by introducing, as a structure constituting a repeating unit of an epoxy resin structure, an aromatic polycyclic structure, in which two aromatic hydrocarbons are bonded through carbon atoms or oxygen atoms in two adjacent substitution positions on an aromatic ring in the aromatic hydrocarbon, into the epoxy resin structure. Thus, the present invention has been completed.

The present invention relates to an epoxy resin composition comprising an epoxy resin and a curing agent, wherein the epoxy resin has an aromatic polycyclic structure in which two aromatic hydrocarbons are bonded through carbon atoms or oxygen atoms in two adjacent substitution positions on an aromatic ring in the aromatic hydrocarbon, and also has glycidyloxy groups as a substituent on the aromatic polycyclic structure.

Another aspect of the invention relates to a novel epoxy resin represented by the general formula (1):

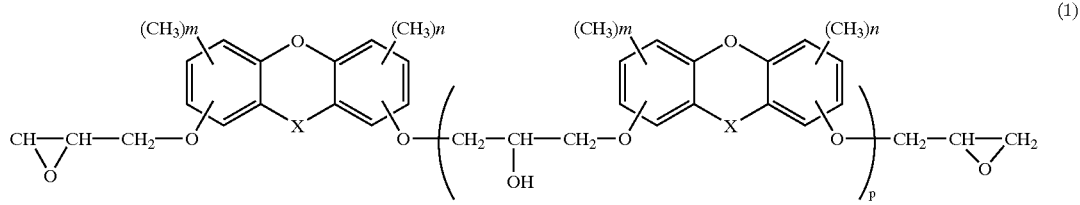

in the general formula (1), X represents oxygen atom, a methylene group, a methylene group substituted with an alkyl group having 1 to 4 carbon atoms, a methylene group substituted with a phenyl group, a methylene group substituted with a naphthyl group, a methylene group substituted with a biphenyl group, a methylene group substituted with a 9-fluorenyl group, or a methylene group in which an alkyl group is further aromatic nucleus-substituted on the phenyl group, the naphthyl group or the biphenyl group, n and m represent an integer of 0 to 3, and p represents an average repeated unit number of 0 to 10.

Still another aspect of the invention relates to a novel epoxy resin represented by the general formula (2):

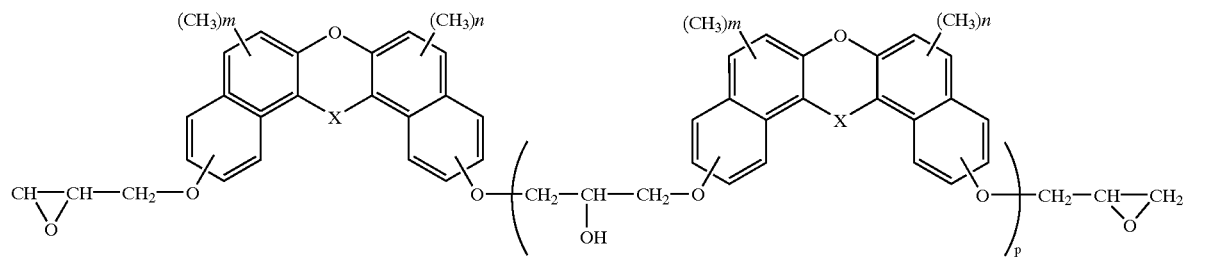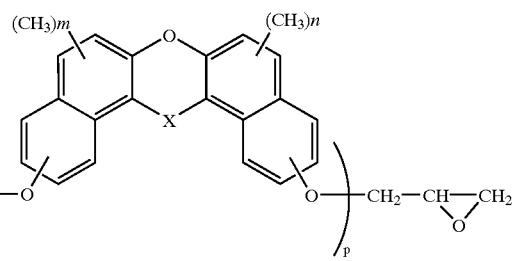

(2)

in the general formula (2), X represents oxygen atom, a methylene group, a methylene group substituted with an alkyl group having 1 to 4 carbon atoms, a methylene group substituted with a phenyl group, a methylene group substituted with a naphthyl group, a methylene group substituted with a biphenyl group, a methylene group substituted with a 9-fluorenyl group, or a methylene group in which an alkyl group is further aromatic nucleus-substituted on the phenyl group, the naphthyl group or the biphenyl group, n and m represents an integer of 0 to 5, and p represents an average repeated unit number of 0 to 10.

A further aspect of the invention relates to a novel phenol compound represented by the general formula (3):

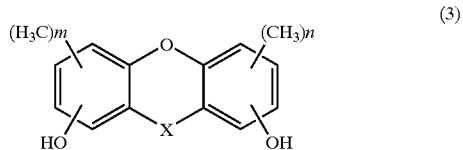

(3)

in the general formula (3), X represents oxygen atom, a methylene group, a methylene group substituted with an alkyl group, a methylene group substituted with a phenyl group, a methylene group substituted with a naphthyl group, a methylene group substituted with a biphenyl group, a methylene group substituted with a 9-fluorenyl group, or a methylene group in which an alkyl group is further aromatic nucleus-substituted on the phenyl group, the naphthyl group or the biphenyl group, and n and m represent an integer of 0 to 3.

A still further aspect of the invention relates to a novel phenol compound represented by the general formula (4):

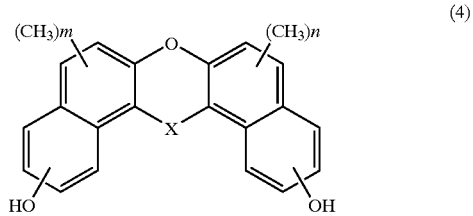

(4)

in the general formula (4), X represents oxygen atom, a methylene group, a methylene group substituted with an alkyl group, a methylene group substituted with a phenyl group, a methylene group substituted with a naphthyl group, a methylene group substituted with a biphenyl group, a methylene group substituted with a 9-fluorenyl group, or a methylene group in which an alkyl group is further aromatic nucleus-substituted on the phenyl group, the naphthyl group or the biphenyl group, and n and m represent an integer of 0 to 5.

Another aspect of the invention relates to a process for preparing a polyhydric hydroxy compound, which comprises reacting a compound having two hydroxyl groups on the benzene ring, one of the hydroxyl groups having a hydrogen atom at the ortho-position and a substituent at all of the other substitution positions, with a carbonyl group-containing compound in the presence of an acid catalyst.

A further invention relates to a cured article obtained by thermally curing the epoxy composition.

DETAILED DESCRIPTION OF THE PREFERRED EMBODIMENTS

Figure 1:
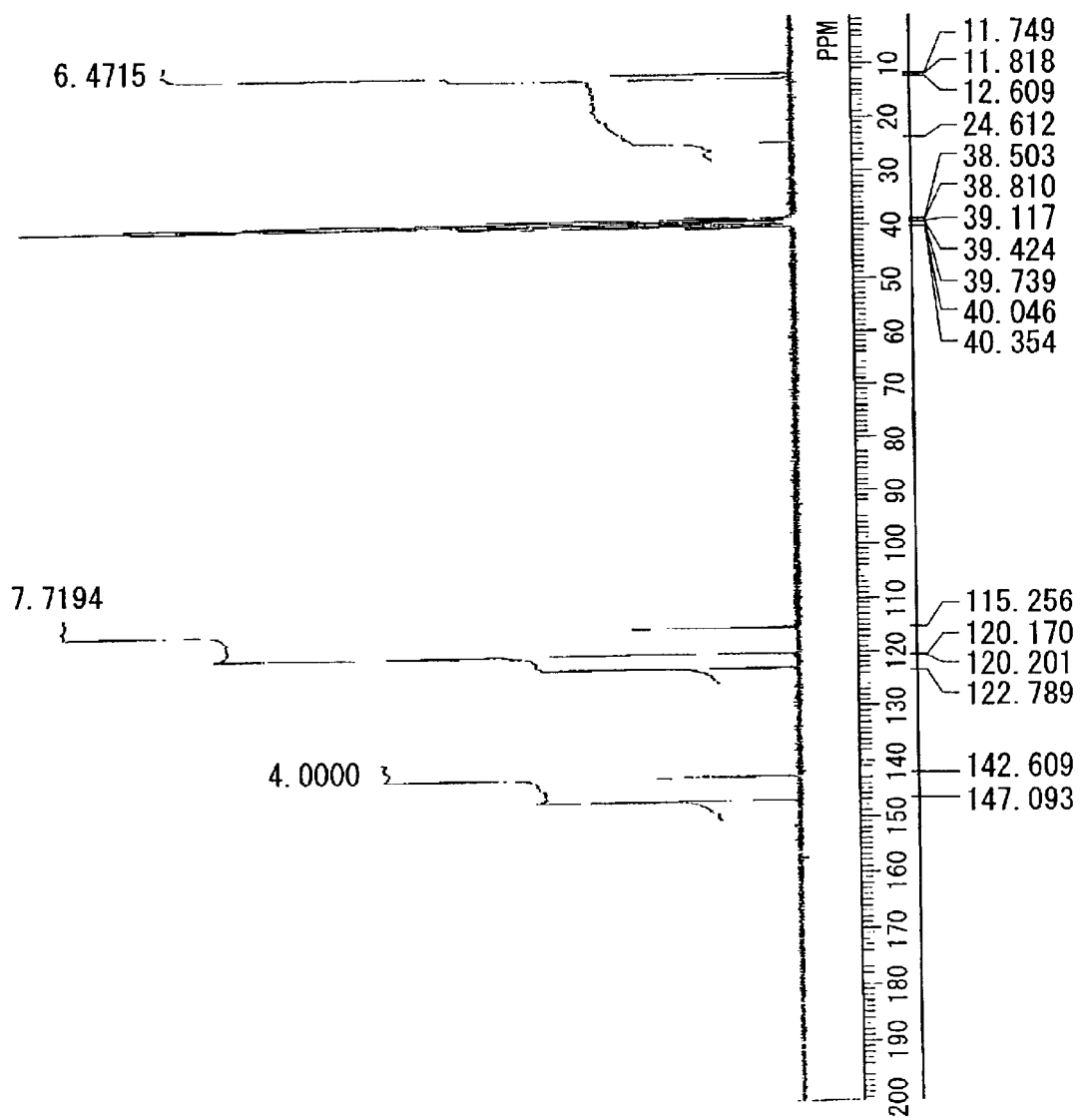
FIG. 1 is a graph showing a $^{13}$C NMR spectrum of a polyhydric hydroxy compound obtained in Example 1.

The present invention will now be described in detail.

The epoxy resin used in the epoxy resin composition of the present invention has an aromatic polycyclic structure in which two aromatic hydrocarbons are bonded through carbon atoms or oxygen atoms in two adjacent substitution positions on an aromatic ring in the aromatic hydrocarbon, and also has glycidyloxy groups as a substituent on the aromatic polycyclic structure.

Since the aromatic content is increased while reducing the epoxy group concentration in the epoxy resin by introducing such a rigid and symmetric structure into the epoxy resin structure, not only are the moisture resistance and the dielectric properties are excellent, but also excellent flame-resistant effects can be exerted. Because of the stiffness of the structure, the heat resistance is also markedly improved.

Specific examples of the aromatic polycyclic structure portion include the following structures. Each line segment drawn from the aromatic ring in the following structural formulas denotes a covalent bond with the other structure portion.

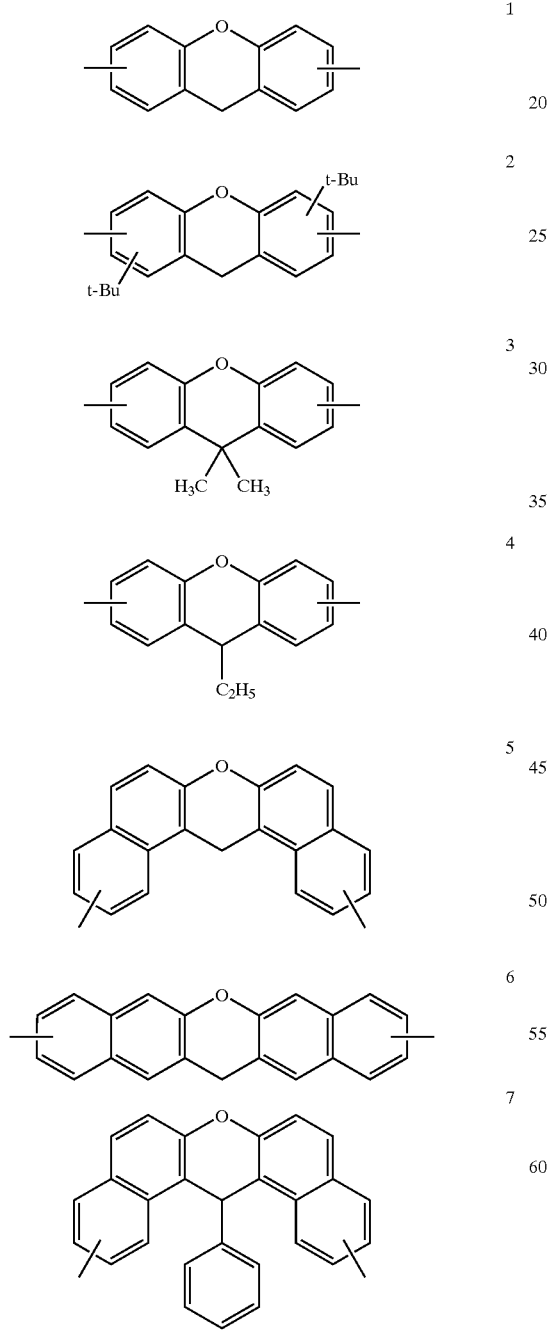

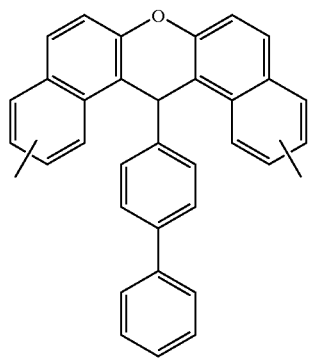

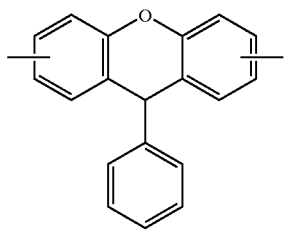

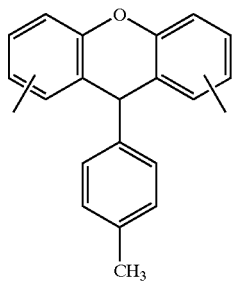

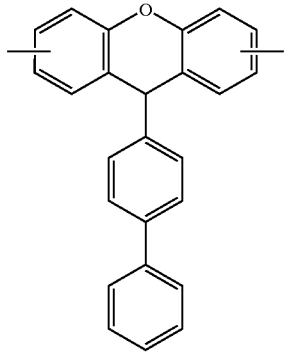

12
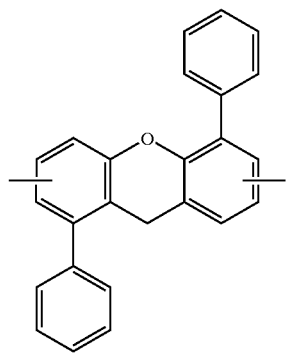
13
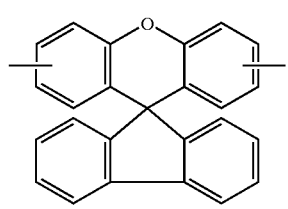
14
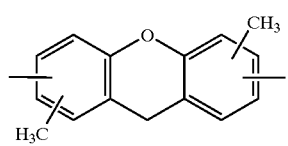
15
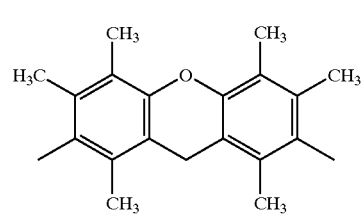
16
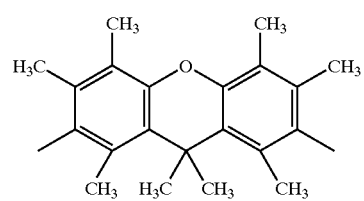
17
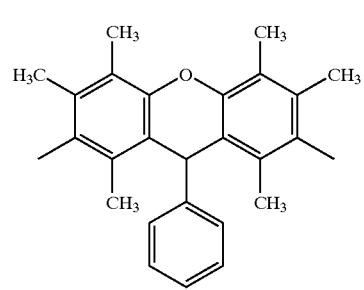
18
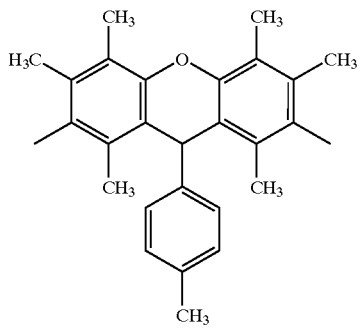
19
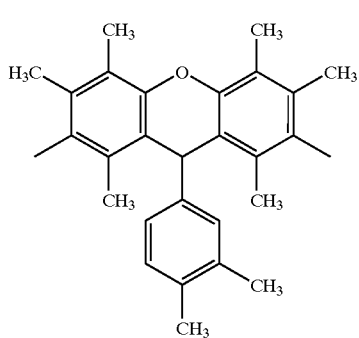
20
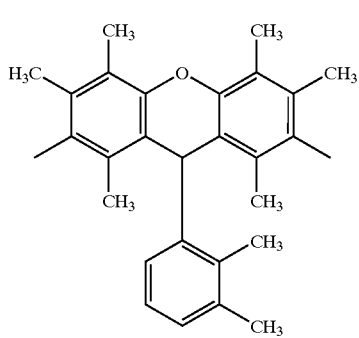
21
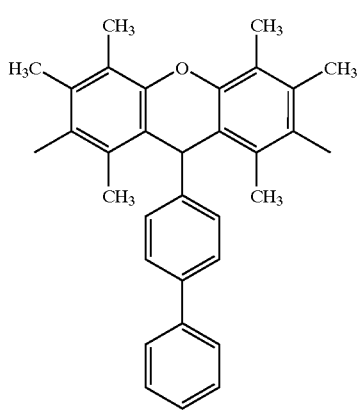

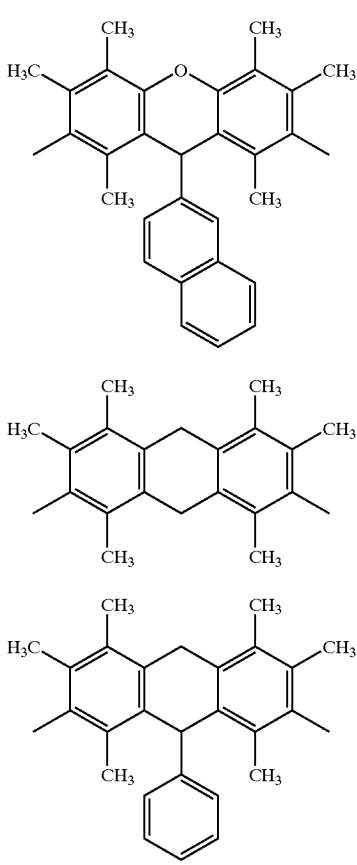

Among these, compounds having methyl groups on the aromatic nucleus, for example, compounds having structures 14 to 24, or compounds wherein an aromatic hydrocarbon is naphthalene, for examples, compounds having structures of 5 to 8 are particularly preferred because the flame-resistant effect is markedly improved.

Although the epoxy resin in the epoxy resin composition of the present invention has the above aromatic polycyclic structure portion as the repeating unit, the epoxy resin may partially contain an aromatic structure having the other structure. Alternatively, an epoxy resin having the other aromatic ring may be used in combination. Since the effect of the present invention is sufficiently exerted, the epoxy resin component preferably contains at least a given amount of the aromatic polycyclic structure portion. Specifically, in the former case, the number of carbon atoms constituting the aromatic polycyclic structure portion accounts for 20% or more of the number of aromatic carbon atoms in the epoxy resin. In the latter case, the number of carbon atoms constituting the aromatic polycyclic structure portion accounts for 20% of the number of aromatic carbon atoms in the entire epoxy resin component in the epoxy resin composition.

The epoxy resin has such a feature that it is superior in moisture resistance and dielectric properties while having comparatively high epoxy equivalent. Therefore, an epoxy resin having an epoxy equivalent within a range from 240 to 330 g/eq. is preferred in view of a good balance between the moisture resistance, the dielectric properties and the flame resistance.

The novel epoxy resin represented by the structural formula 1 or the novel epoxy resin represented by the structural formula 2 is suited for use as the epoxy resin.

These novel resins of the present invention will now be described in detail.

The novel epoxy resin of the present invention is represented by the general formula (1).

Among the novel epoxy resins represented by the general formula (1), an epoxy resin having methyl groups in the aromatic polycyclic structure, namely, an epoxy resin having a structure of the general formula (1) wherein n and m represent 1 to 3 is particularly preferred. Specific examples of the repeating unit constituting such an epoxy resin include the following.

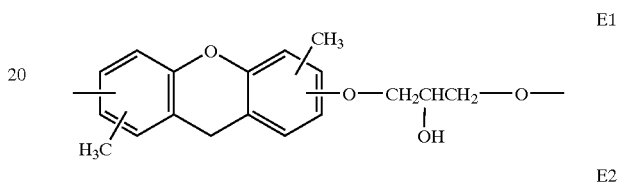

E1

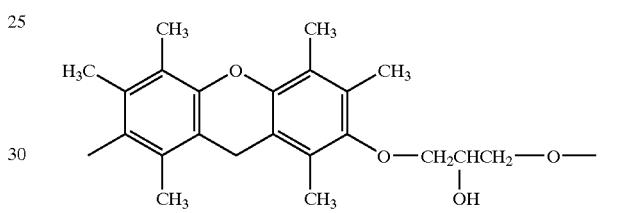

E2

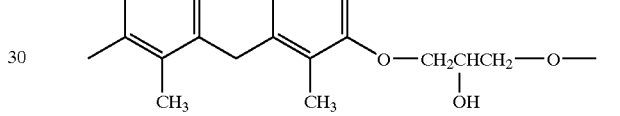

E3

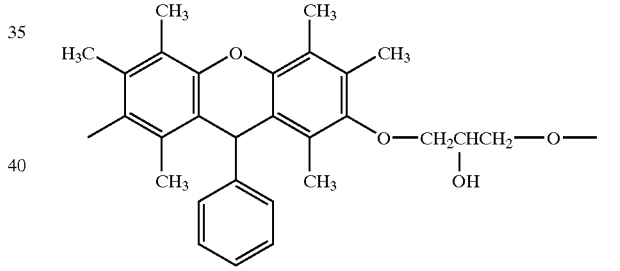

E4

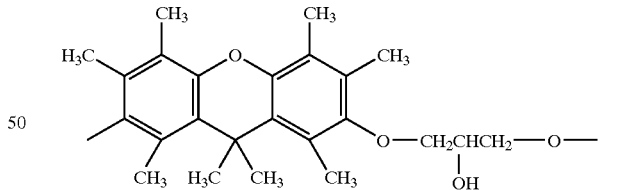

E5

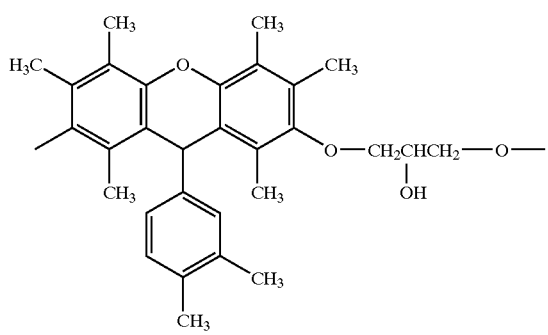

E6

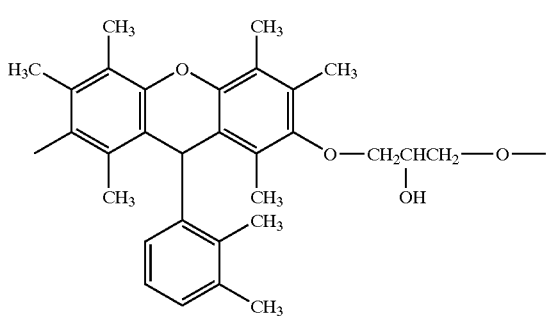

E7

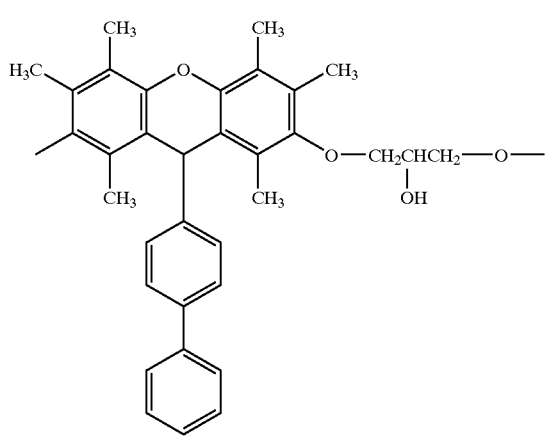

E8

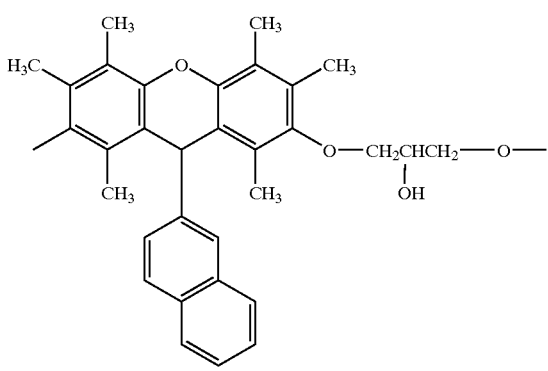

E9

Among these, compounds having three methyl groups in the benzene ring constituting the aromatic polycyclic structure portion, for example, compounds having structures E2 to E9, are preferred because they are easy to industrially manufacture and are markedly superior in effect of improving the heat resistance and the flame resistance. Compounds having structures E2 and E3 are preferred because they are markedly superior in heat resistance, while compounds having structures E1, E2, E3 and E4 are preferred because they are satisfactory in fluidity and compounds having structures E7 and E8 are preferred because they are markedly superior in flame resistance, dielectric properties and moisture resistance.

The novel epoxy resin having a naphthalene skeleton of the present invention is represented by the general formula (2).

Specific examples of the repeating unit constituting the epoxy resin include the following.

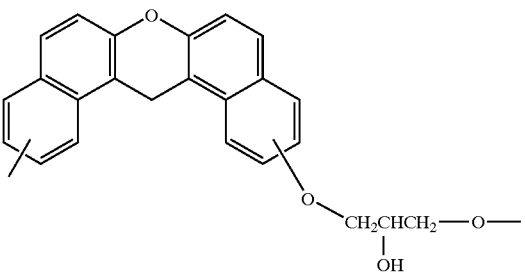

E10

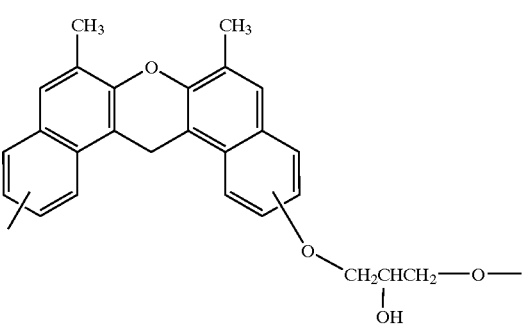

E11

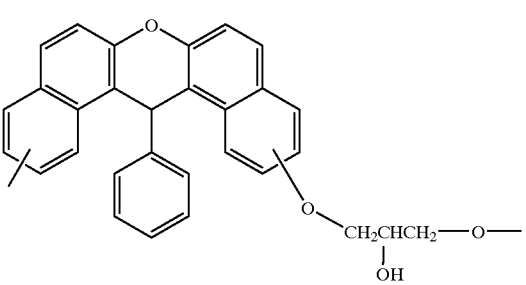

E12

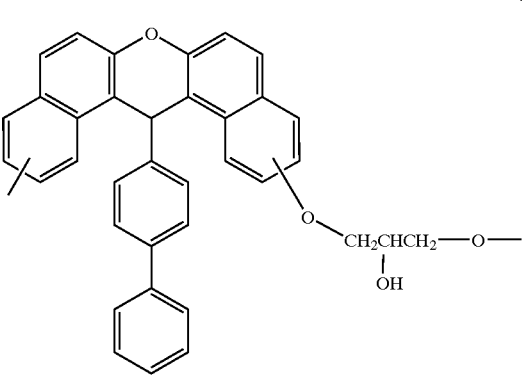

E13

In the novel epoxy resin represented by the general formula (1) or (2), since the epoxy resin has a high epoxy group equivalent, the flame-resistant effect of the cured article is enhanced. When the epoxy group equivalent is high, the heat resistance is usually lowered with a reduction in crosslink density. However, in the case of the present invention, no lowering in heat resistance is observed regardless of a relative increase in epoxy equivalent, and markedly excellent heat resistance is exerted. The epoxy equivalent is preferably within a range from 240 to 330 g/eq. because such a feature becomes more remarkable.

As described above, the value of p, which denotes the average value of the repeating number in the general formulas (1) and (2), is within a range from 0 to 10, but can be arbitrarily adjusted depending on the desired properties. To enhance the fluidity of the composition and the heat resistance of the cured article, the average value p is preferably within a range from 0 to 1. To improve the operatability by increasing the softening point of the composition, the average value p is preferably within a range from 1 to 5.

Furthermore, the flame-resistant effect of the novel epoxy resin of the present invention is markedly improved by introducing methyl groups onto the aromatic nucleus. A remarkable point is that the flame-resistant effect of the cured article is markedly improved regardless of the numerous alkyl groups that are easy to burn.

The novel epoxy resin of the present invention can be prepared by preparing a novel phenol compound of the present invention as an intermediate thereof and subjecting the resulting novel phenol compound to glycidyl etherification.

The novel phenol compound of the present invention will now be described in detail.

The novel phenol compound of the present invention is represented by the general formula (3).

Specific examples of the novel phenol compound include those having the following structures.

P1
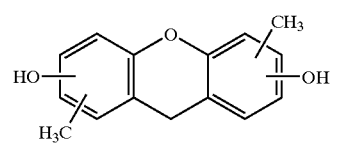

P2
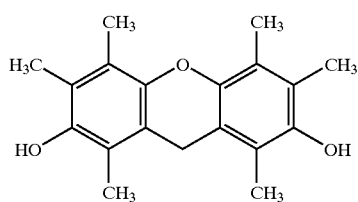

P3
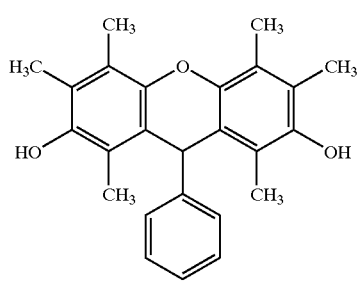

-continued

P4
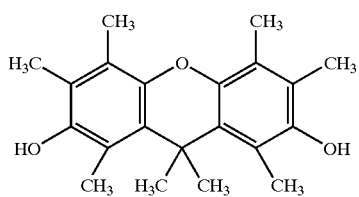

P5
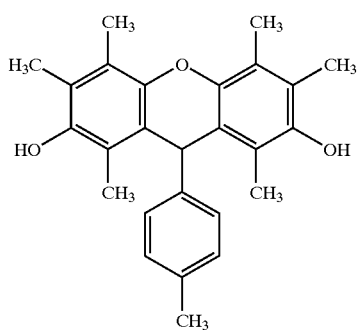

P6
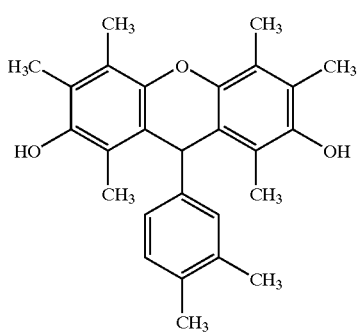

P7
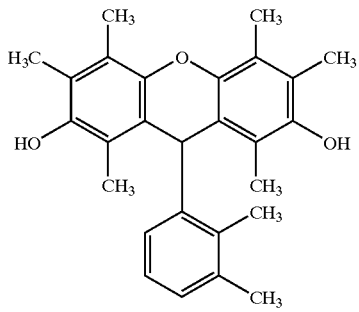

P8
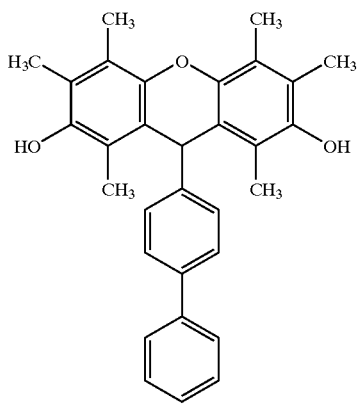

-continued

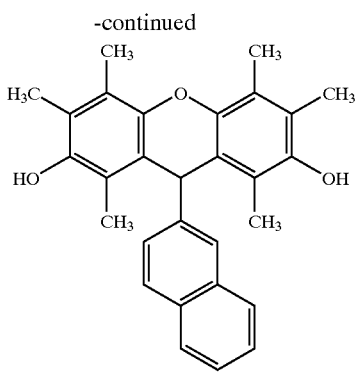

P9

Another novel phenol compound of the present invention is represented by the general formula (4).

Specific examples of the novel phenol compound include those having the following structures.

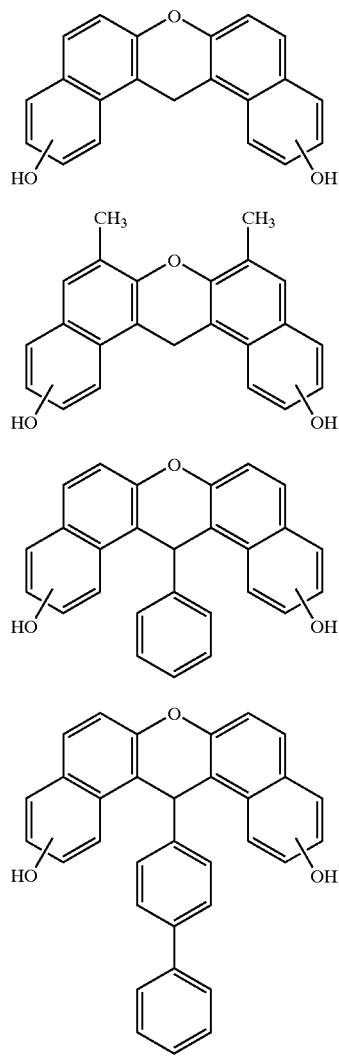

P10

P11

P12

P13

The novel phenol compound represented by the general formula (3) or (4) is very useful as an intermediate of the novel epoxy resin of the present invention, but can be used in various purposes because of its rigid and symmetric structure, and thus the heat resistance and the flame resistance can be improved. Specifically, the novel phenol compound can be used as raw materials of epoxy resin curing agents and vinyl ester resins, raw materials of photosensitive materials such as photoresists for semiconductors, and raw materials polycarbonate resins, polyester resins and polyarylate resins.

The novel phenol compound represented by the general formula (3) or (4) can be prepared by reacting dihydroxybenzene having hydrogen atoms at the position adjacent to hydroxyl groups or dihydroxynaphthalene having hydrogen atoms at the position adjacent to hydroxyl groups with a carbonyl group-containing compound in the presence of an acid catalyst. In this case, when a phenol compound having the other structure is produced as a by-product, the desired compound may be isolated by a purification means such as recrystallization.

Examples of the dihydroxybenzene having hydrogen atoms at the position adjacent to hydroxyl groups include hydroquinone, monomethylhydroquinone, trimethylhydroquinone, trimethylresorcin, and trimethylcatechol, while examples of dihydroxynaphthalene having hydrogen atoms at the position adjacent to hydroxyl groups include 1,6-dihydroxynaphthalene, 2,7-dihydroxynaphthalene, and 1,6-dihydroxy-7-methylnaphthalene.

In the process for preparing the phenol compound of the present invention, the compound having two hydroxyl groups on the benzene ring, one of the hydroxyl groups having hydrogen atom at the ortho-position and a substituent at all of other substitution positions, is used as the dihydroxybenzene. According to the process of the present invention, the novel phenol compound represented by the general formula (3) can be prepared in high purity.

Specific examples of the compound having two hydroxyl groups on the benzene ring, one of the hydroxyl groups having a hydrogen atom at the ortho-position and a substituent at all of other substitution positions, include trimethylhydroquinone, trimethylresorcin, and trimethylcatechol. In addition, trimethylhydroquinone, tri-t-butylhydroquinone, tribromohydroquinone and trichlorohydroquinone can be used.

Various carbonyl group-containing compounds can be used to react with the compound described above. Depending on the kind of the carbonyl group-containing compound, various structures can be introduced into the novel phenol compound, thereby making it possible to impart various performances to the novel phenol compound.

Specific examples thereof include aldehyde compounds such as formaldehyde, acetaldehyde, benzaldehyde, 4-methylbenzaldehyde, 3,4-dimethylbenzaldehyde, biphenylaldehyde, and naphthylaldehyde; and ketone compounds such as benzophenone, fluorenone, and indanone. Among these compounds, benzaldehyde, 4-methylbenzaldehyde, 3,4-dimethylbenzaldehyde, biphenylaldehyde and naphthylaldehyde are preferred to remarkably enhance the flame resistance of the epoxy resin intermediate.

An acid catalyst is used as a reaction catalyst. To prepare the novel phenol compound in high purity, strong acids such as hydrochloric acid, sulfuric acid, paratoluenesulfonic acid, and methanesulfonic acid are used as the catalyst.

The reaction between the dihydroxybenzene having hydrogen atoms at the position adjacent to hydroxyl groups or dihydroxynaphthalene having hydrogen atoms at the position adjacent to hydroxyl groups and the carbonyl group-containing compound is completed through the first stage of bonding dihydroxytrimethylbenzenes with each other through methylene by means of the condensation reaction between dihydroxytrimethylbenzene or dihydroxynaphthalene and the carbonyl group-containing compound, and the second stage of forming a 6-membered ring ether skeleton by means of the dehydration condensation between hydroxyl groups. For example, the reactions of the first and second stage proceed as shown in the following schemes (1) and (2) in the reaction between trimethylhydroquinone and formaldehyde.

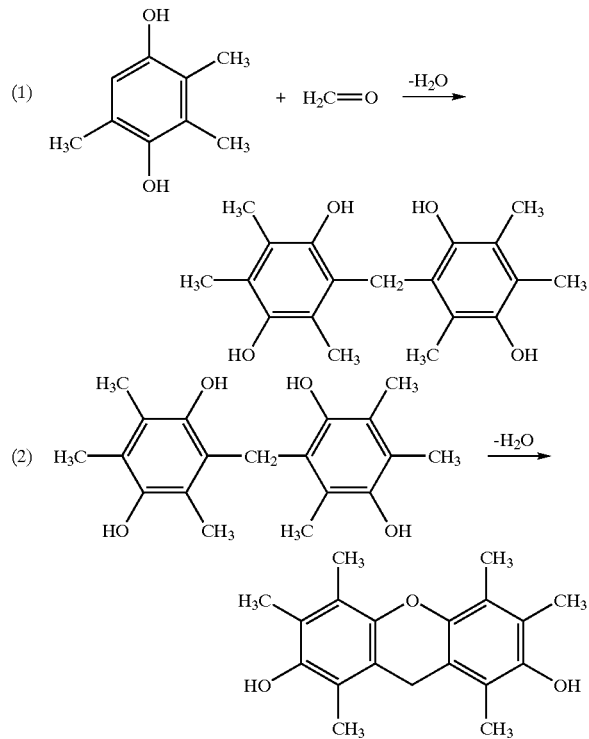

These reaction conditions may be such that the two-stage successive reaction proceeds to form the desired skeleton. Specifically, 1 mol of dihydroxybenzene or dihydroxynaphthalene is reacted with 0.1 to 3.0 mol of the carbonyl group-containing compound and the reaction temperature is particularly preferably within a range from 50 to 200° C. because the yield of the desired product and the purity in the reaction product are enhanced.

Since these reaction conditions enhance the yield of the desired product and the purity in the reaction product, it is particularly preferred that 1 mol of dihydroxybenzene or dihydroxynaphthalene be reacted with 0.4 to 0.7 mol of the carbonyl group-containing compound and that the reaction temperature be particularly preferably within a range from 100 to 150° C.

The reaction is preferably conducted by dissolving raw materials in a proper organic solvent such as toluene, benzene, ethylene glycol, or a mixed solvent thereof. Since the reaction of the second stage is a dehydration reaction, the reaction is preferably conducted while removing water formed during the reaction.

The novel epoxy resin of the present invention can be obtained by adding an alkali metal hydroxide such as sodium hydroxide or potassium hydroxide to a mixture of the novel phenol compound thus obtained of the present invention dissolved in epihalohydrins such as epichlorohydrin, epibromohydrin, or á-methylepichlorohydrin, and reacting them or reacting while adding the alkali metal hydroxide at 20 to 120° C. for 1 to 10 hours.

The amount of epihalohydrins is usually within a range from 0.3 to 20 equivalent based on 1 equivalent of hydroxyl groups in the phenol resin of the raw material. When the amount of epihalohydrins is smaller than 2.5 equivalent, a high-molecular weight compound having secondary hydroxyl groups formed by the addition reaction between epoxy groups and unreacted hydroxyl groups is obtained. On the other hand, when the amount is larger 2.5 equivalent, the content of a low-molecular weight compound increases.

In the reaction between the novel phenol compound and epihalohydrins, the alkali metal hydroxide is used in the form of an aqueous solution. In that case, there can be used a process of continuously adding the aqueous solution of the alkali metal hydroxide in the reaction system, continuously distilling off water and epihalohydrin under reduced pressure or normal pressure, separating the solution into water and epihalohydrins, removing water and continuously returning epihalohydrins in the reaction system.

The epoxy resin of the present invention can also be prepared by adding, as a catalyst, a quaternary ammonium salt such as tetramethylammonium chloride, tetramethylammonium chloride, or tetramethylbenzylammonium chloride to the mixture of the novel phenol compound dissolved in epihalohydrins, reacting at 50 to 150° C. for 1 to 5 hours, adding a solid or an aqueous solution of an alkali metal hydroxide to a halohydrin etherified compound of the resulting phenol resin, reacting again at 20 to 120° C. for 1 to 10 hours, thereby to cause dehydrohalogenation (ring closure).

In these reactions, the reaction is preferably conducted by adding alcohols such as methanol, ethanol, isopropyl alcohol, and butanol; ketones such as acetone and methyl ethyl ketone; ethers such as dioxane; and aprotic polar solvents such as dimethylsulfone and dimethyl sulfoxide so as to allow the reaction to smoothly proceed. When using the solvent, the amount is usually within a range from 5 to 50 parts by weight, and preferably 10 to 30 parts by weight, based on 100 parts by weight of epihalohydrins. When using the aprotic polar solvent, the amount is usually within a range from 5 to 100 parts by weight, and preferably 10 to 60 parts by weight, based on 100 parts by weight of epihalohydrins.

After the completion of the epoxidation reaction, the reaction product is washed with water or not, and then epihalohydrins and other solvents added are removed with heating to 110 to 250° C. under reduced pressure of 10 mmHg or less to obtain a crude epoxy resin.

To obtain an epoxy resin containing less hydrolyzable halogen, the crude epoxy resin is dissolved again in the solvent such as toluene or methyl isobutyl ketone and, after adding an aqueous solution of an alkali metal hydroxide such as sodium hydroxide or potassium hydroxide, and the mixture is reacted, thereby to ensure the ring closure. In this case, the amount of the alkali metal hydroxide is usually within a range from 0.5 to 10 mol, and preferably from 1.2 to 5.0 mol, based on 1 mol of hydrolyzable chlorine remained in the crude epoxy resin. The reaction temperature is preferably within a range from 50 to 120° C., while the reaction time is preferably within a range from 0.5 to 3 hours. For the purpose of increasing the reaction rate, phase transfer catalysts such as quaternary ammonium salt and crown ether may be added. When using the phase transfer catalyst, the amount is preferably within a range from 0.1 to 3.0 parts by weight based on 100 parts by weight of the crude epoxy resin.

After the completion of the reaction, the salt formed is removed by filtration or washing with water and the solvent such as toluene or methyl isobutyl ketone is distilled off with heating under reduced pressure to obtain a novel epoxy resin of the present invention.

Although the epoxy resin composition of the present invention comprises the epoxy resin having an aromatic polycyclic structure, preferably the novel epoxy resin, and a curing agent, the other epoxy resin may be used in combination in the present invention.

Examples of the epoxy resin, which can be used in combination, include bisphenol A type epoxy resin, bisphenol F type epoxy resin, biphenyl type epoxy resin, tetramethylbiphenyl type epoxy resin, phenol novolak type epoxy resin, cresol novolak type epoxy resin, triphenylmethane type epoxy resin, triphenylethane type epoxy resin, dicyclopentadiene-phenol addition reaction type epoxy resin, phenol aralkyl type epoxy resin, naphthol novolak type epoxy resin, naphthol aralkyl type epoxy resin, naphthol-phenol cocondensation type epoxy resin, naphthol-cresol cocondensation type epoxy resin, aromatic hydrocarbonformaldehyde resin-modified phenol resin type epoxy resin, biphenyl-modified novolak type epoxy resin, tetrabromobisphenol A type epoxy resin, and brominated phenol novolak type epoxy resin. Among these epoxy resins, bisphenol A type epoxy resin, bisphenol F type epoxy resin, biphenyl type epoxy resin, tetramethylbiphenyl type epoxy resin and dicyclopentadiene-phenol addition reaction type epoxy resin are particularly preferred in view of the fluidity.

The amount of these epoxy resins, which can be used in combination, is preferably 20% by weight or less based on the entire epoxy resin component in the composition.

Various curing agents for epoxy resin can be used as the curing agent in the epoxy resin composition of the present invention and examples thereof include curing agents for epoxy resin, such as amine-based compound, acid anhydride-based compound, amide-based compound, and phenol-based compound.

Specific examples thereof include polyhydric phenol compounds such as diaminodiphenylmethane, diethylenetriamine, triethylenetetramine, diaminodiphenolsulfone, isophoronediamine, dicyandiamide, polyamide resin synthesized from a dimer of linolenic acid and ethylenediamine, phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, methylhexahydrophthalic anhydride, phenol novolak resin, cresol novolak resin, aromatic hydrocarbonformaldehyde resin-modified phenol resin, dicyclopentadiene phenol addition type resin, phenolaralkyl resin, cresol aralkyl resin, naphthol aralkyl resin, biphenol-modified phenolaralkyl resin, phenoltrimethylolmethane resin, tetraphenylolethane resin, naphthol novolak resin, naphthol-phenol cocondensation resin, naphthol-cresol cocondensation resin, biphenol-modified phenol resin and aminotriazine-modified phenol resin; modified compounds thereof; imidazoles; $BF_3$-amine complexes; and guanidine derivatives. These curing agents may be used alone, or two or more kinds thereof may be used in combination.

Among these curing agents, phenol novolak resin, naphthol novolak resin and phenoltrimethylolmethane resin are particularly preferred in view of excellent heat resistance. In view of excellent moisture resistance, phenolaralkyl resin, cresol aralkyl resin, naphthol aralkyl resin and biphenol-modified phenol aralkyl resin are particularly preferred. In view of excellent flame resistance, phenolaralkyl resin, cresol aralkyl resin, naphthol aralkyl resin, biphenol-modified phenolaralkyl resin and aminotriazine-modified phenol resin are particularly preferred.

Examples of the phenolaralkyl resin, the naphthol aralkyl resin and the biphenol-modified phenolaralkyl resin include those represented by the following general formula (5) or (6).

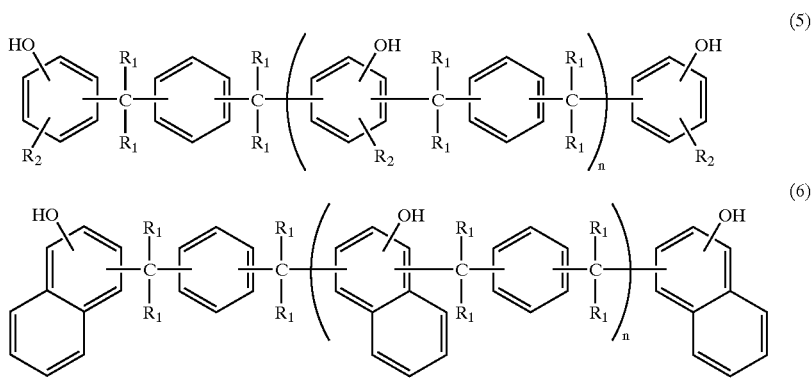

In the above formula, $R_1$ each independently represents hydrogen atom, a methyl group or an ethyl group, and $R_2$ represents hydrogen atom or a methyl group. Also n is an average value and represents within a range from 0 to 10.

With respect to the amount of the curing agent, the amount of the active hydrogen group in the curing agent is preferably within a range from 0.7 to 1.5 equivalent based on 1 equivalent of the epoxy group of the epoxy resin because sufficient curing reaction occurs and curing physical properties becomes satisfactory.

Curing accelerators can be appropriately used. Any of conventionally known curing accelerators can be used and examples thereof include phosphorus-based compound, tertiary amine, imidazole, organic acid metal salt, Lewis acid, and amine complex salt. A phosphorus-based compound such as triphenylphosphine and a tertiary amine such as 1,8-diazabicyclo-[5,4,0]-undecene (DBU) are preferably used in semiconductor encapsulating materials because of excellent curability, heat resistance, electric properties, and moisture resistance reliability.

In addition to the respective components described above, inorganic fillers are preferably added to the epoxy resin composition of the present invention. Particularly, these inorganic fillers are essential components in semiconductor encapsulating materials. Specific examples of the inorganic filler include fumed silica, crystalline silica, alumina, silicon nitride, and aluminum nitride.

When the amount of the inorganic filler is particularly increased, fumed silica is preferably used. Although ground or spherical fumed silica can be used, spherical fumed silica is preferably used in order to increase fumed silica and suppress an increase in melt viscosity of a molding material. To increase the amount of spherical silica, it is preferably controlled so that the particle size distribution of spherical silica is broader.

If necessary, various additives such as silane coupling agents, releasants and pigment can be added.

In the epoxy resin composition of the present invention, since the epoxy resin itself as a main component has excellent flame resistance, the use of flame resistance imparting agents such as halogen compound is not required. In this case, the resulting flame-resistant composition substantially contains no halogen compound.

However, when the halogen compound and the other flame resistance imparting agent can be used in combination depending on the purposes, the flame resistance imparting agent may be used optionally to further improve the flame-resistant effect. As the flame resistance imparting agent, for example, a halogen compound, a phosphorus atom-containing compound, a nitrogen atom-containing compound and an inorganic flame-resistant compound are listed. Specific examples thereof include halogen compound such as tetrabromobisphenol A type epoxy resin, phosphorus atom-containing compound such as red phosphorus or phosphate ester compound, nitrogen atom-containing compound such as melamine, and inorganic flame-resistant compound such as aluminum hydroxide, magnesium hydroxide, zinc borate or calcium borate.

The epoxy resin composition of the present invention can be obtained by uniformly mixing the respective components described above. The epoxy resin composition of the present invention can be applied to various purposes to which the flame resistance and the heat resistance are required, but is useful as electric or electronic materials, particularly semiconductor encapsulating materials and varnishes for circuit boards, as described above.

The semiconductor encapsulating material can be prepared by sufficiently mixing an epoxy resin, a curing agent, an inorganic filler and, if necessary, other components using an extruder, a kneader or a roll until a uniform mixture can be obtained. Silica is preferably used as the filler. The amount of the inorganic filler is usually an amount which allows a filling factor to be set within a range from 30 to 95% by weight. To improve the flame resistance, the moisture resistance and the solder cracking resistance and to reduce a coefficient of linear expansion, the filling factor is preferably 70% by weight or more. To exert a remarkable effect thereof, the filling factor is particularly preferably 80% by weight or more.

The varnish for circuit board material can be prepared by dissolving the epoxy resin composition of the present invention in a solvent such as toluene, xylene, acetone, methyl ethyl ketone or methyl isobutyl ketone. In this case, the amount of the solvent is usually within a range from 10 to 70% by weight, preferably from 15 to 65% by weight, and particularly preferably from 15 to 65% by weight, based on the varnish for circuit board material. Specific examples of the circuit board material include printed wiring boards, printed circuit boards, flexible printed wiring boards, and build-up wiring boards.

The cured article of the present invention can be obtained by thermally curing the epoxy resin composition. The cured article can be used as molded articles, laminates, cast articles, adhesives, coating films and films. For example, the cured article of the semiconductor encapsulating material is a cast article or a molded article, and the cured article used for these purposes can be obtained by molding the composition using a casting, transfer or injection molding machine and heating to a temperature within a range from 80 to 200° C. for 2 to 10 hours. The cured article of the varnish for circuit board is a laminate and this cured article can be obtained by impregnating a base material such as glass fiber, carbon fiber, polyester fiber, polyamide fiber, alumina fiber or paper with the varnish for circuit boards, drying the impregnated base material with heating to form a prepreg, and hot-pressing the prepreg.

EXAMPLES

The present invention will now be described in detail by way of Examples and Comparative Examples.

Example 1

Figure 2:
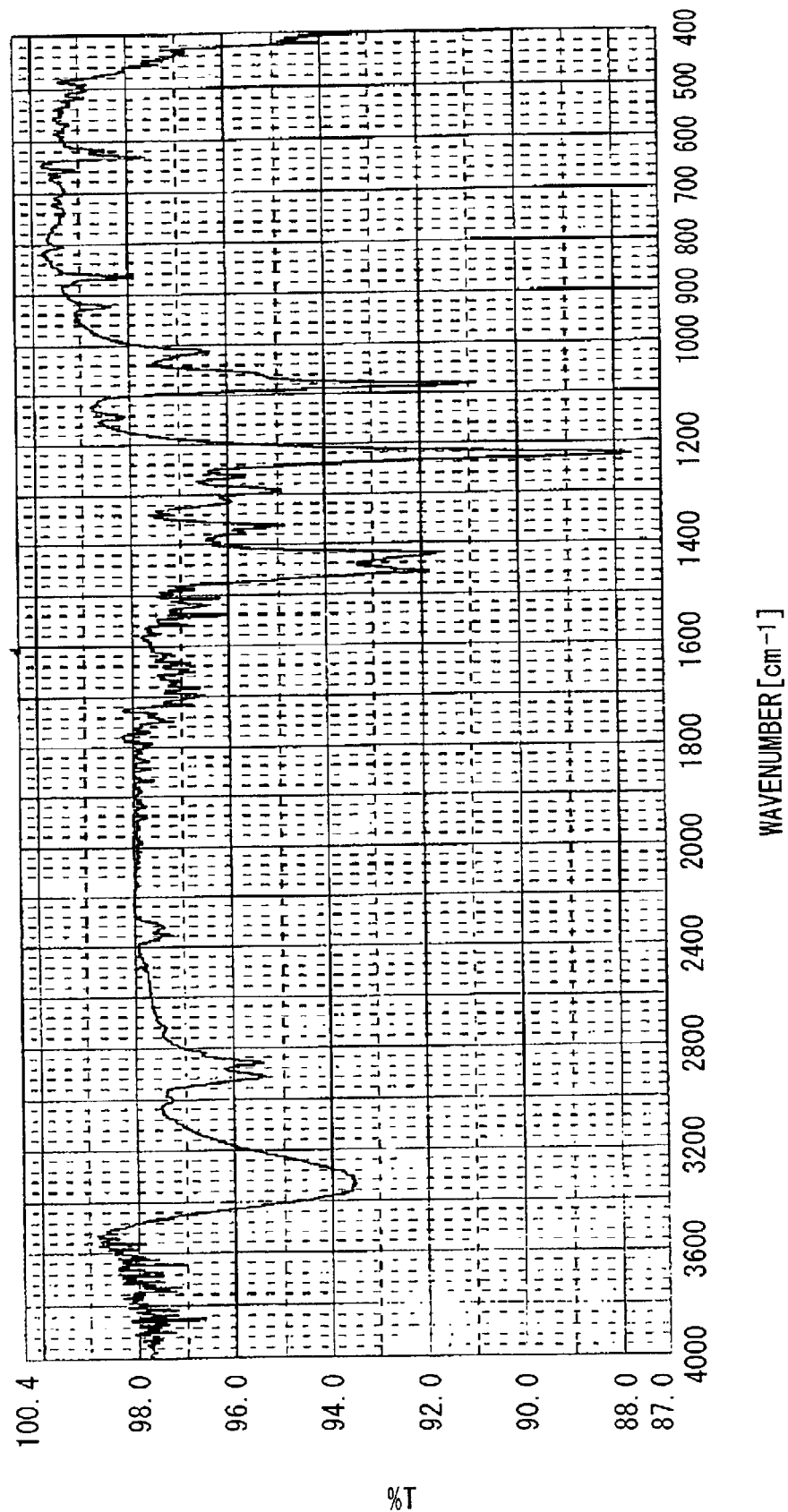
FIG. 2 is a graph showing an IR spectrum of a polyhydric hydroxy compound obtained in Example 1.
Figure 3:
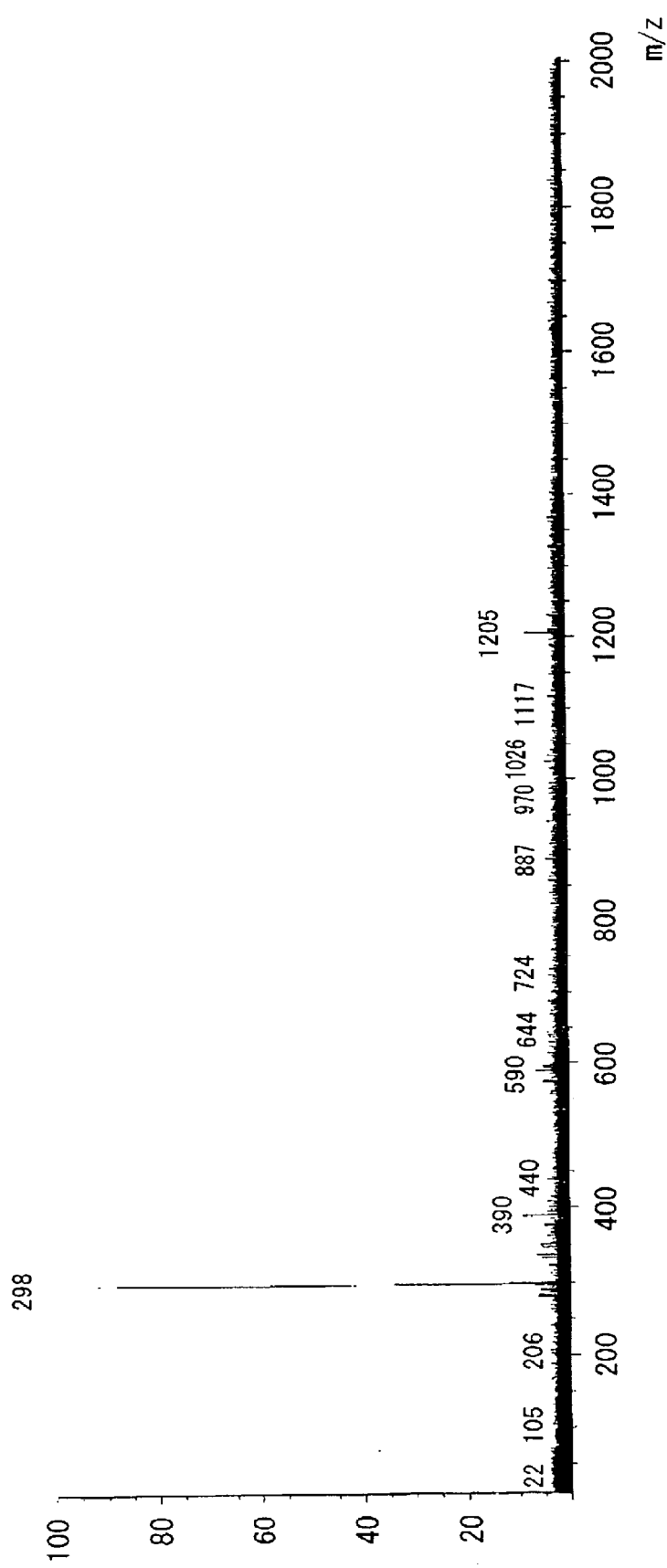
FIG. 3 is a graph showing a mass spectrum of a polyhydric hydroxy compound obtained in Example 1.

In a four-necked flask equipped with a stirrer and a heater, 152 g (1.0 mol) of trimethylhydroquinone was dissolved in a mixed solvent of 500 g of toluene and 200 g of ethylene glycol monoethyl ether. To the solution, 4.6 g of paratoluenesulfonic acid was added and 44 g (0.6 mol) of 41% formalin was added dropwise while taking account of heat generation, followed by stirring at 100 to 120° C. for 15 hours while distilling off moisture. After cooling, the deposited crystal was collected by filtration, washed repeatedly with water until the wash became neutral, and then dried to obtain 132 g (GPC purity: 98%) of a polyhydric hydroxy compound shown below. The structure was identified from a NMR spectrum ($^{13}$C) of FIG. 1, an IR spectrum (KBr) of FIG. 2 and a mass spectrum of FIG. 3.

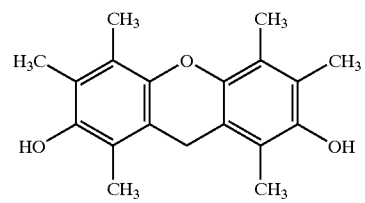

Example 2

In a flask equipped with a thermometer, a dropping funnel, a cooling tube and a stirrer, 149 g of (hydroxyl group: 1.0 equivalent) of the polyhydric hydroxy compound obtained in Example 1, 463 g (5.0 mol) of epichlorohydrin, 53 g of n-butanol and 2.3 g of tetraethylbenztlammonium chloride were charged and dissolved while the atmosphere in the flask was purged with a nitrogen gas. After heating to 650°C., the pressure was reduced to a pressure at which azeotropy occurs, and then 82 g (1.0 mol) of an aqueous 49% sodium hydroxideaqueous solution was added dropwise over 5 hours. Under the same conditions, stirring was continued for 0.5 hours. During stirring, the distillate obtained as a result of azeotropy was separated by a Dean-Stark trap and the aqueous layer was distilled off, and then the reaction was conducted while returning the oil layer into the reaction system. Then, the unreacted epichlorohydrin was distilled off by distillation under reduced pressure. The resulting crude epoxy resin was dissolved by adding 550 g of methyl isobutyl ketone and 55 g of n-butanol. To the solution, 15 g of an aqueous 10% sodium hydroxide solution was added and, after reacting at 80° C. for 2 hours, the reaction solution was washed with 100 g of water three times until the wash became neutral. After dehydration of the system by azeotropy, microfiltration was conducted and the solvent was distilled off under reduced pressure to obtain 188 g of the desired epoxy resin (A) represented by the following structural formula. The epoxy equivalent of the resulting epoxy resin was 227 g/eq. The structure was identified from a NMR spectrum ($^{13}$C) of FIG. 1, an IR spectrum (KBr) of FIG. 2 and a mass spectrum of FIG. 3. It was confirmed by GPC analysis that an average repeated unit number p is 0.1.

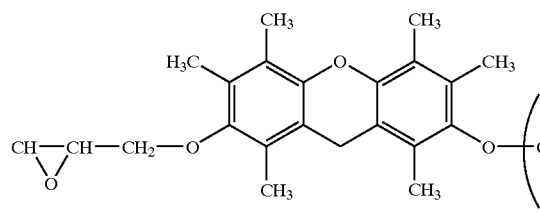

Example 3

Figure 4:
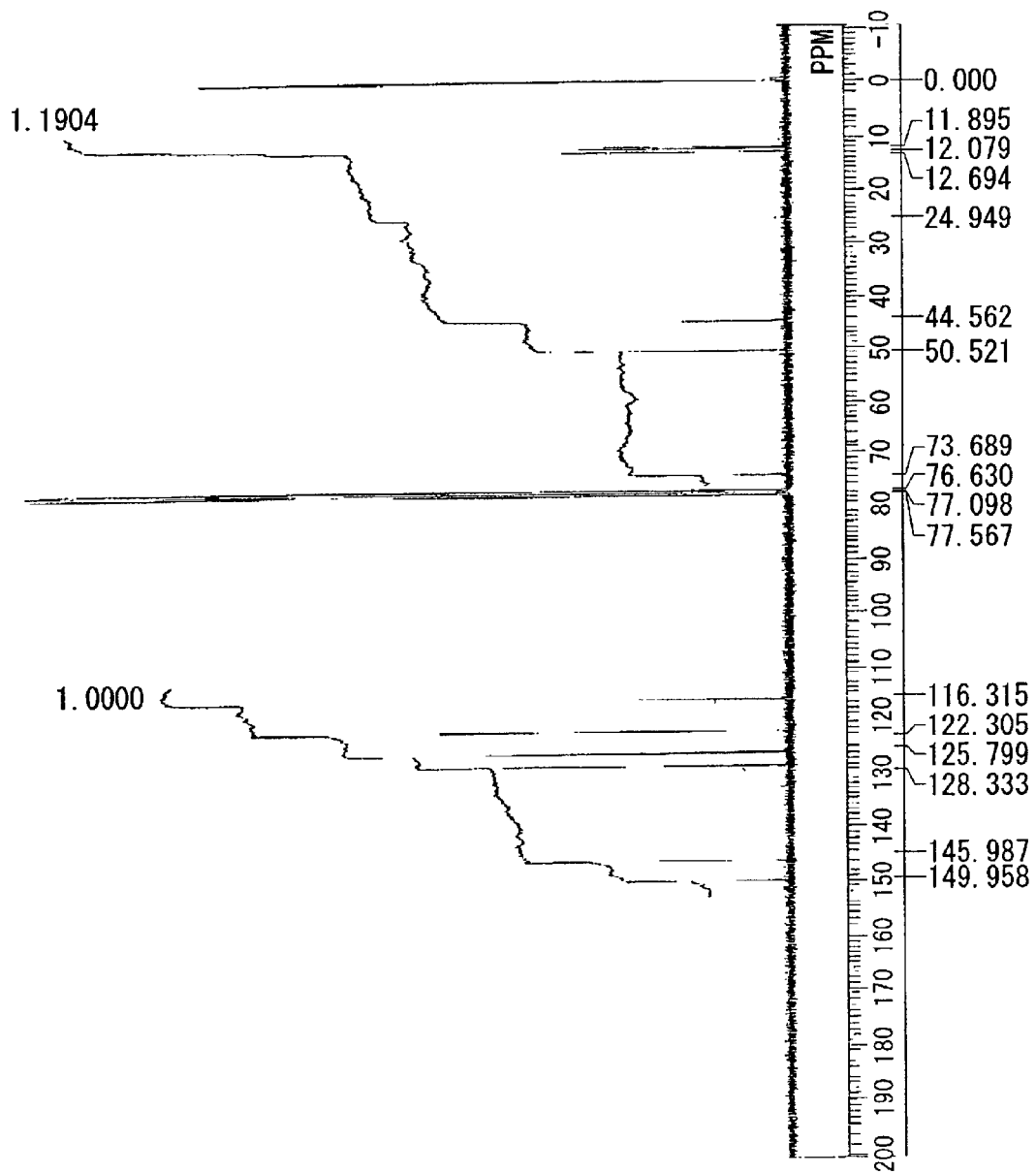
FIG. 4 is a graph showing a $^{13}$C NMR spectrum of an epoxy resin obtained in Example 2.
Figure 5:
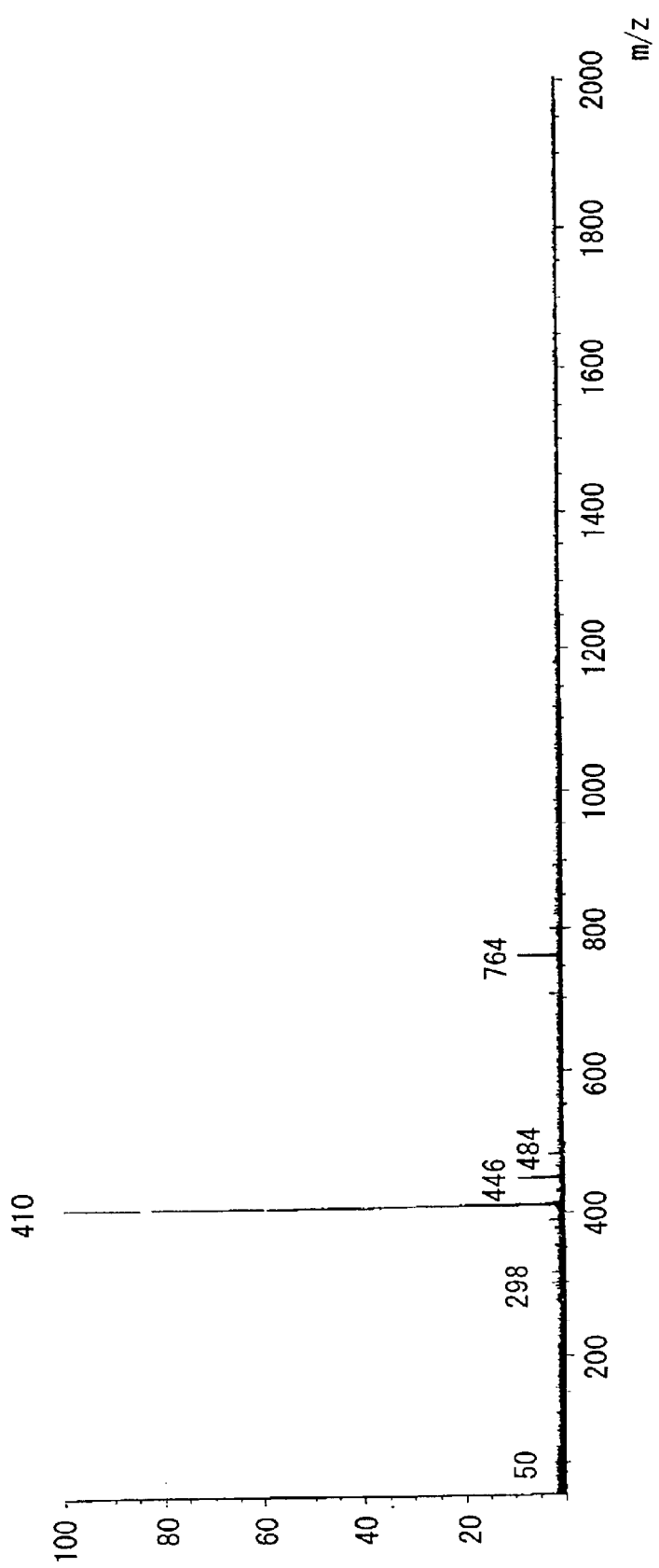
FIG. 5 is a graph showing an IR spectrum of an epoxy resin obtained in Example 2.
Figure 6:
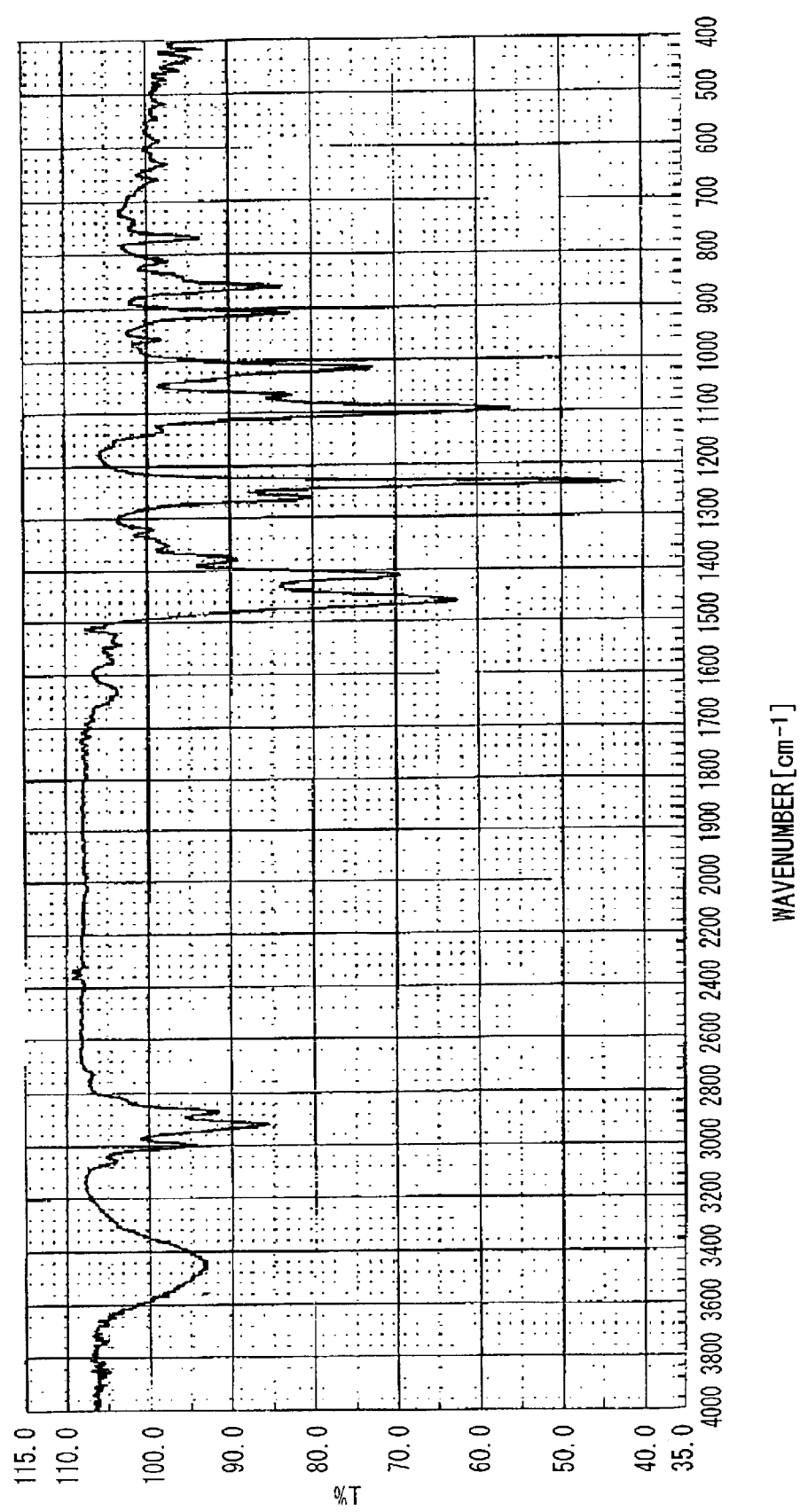
FIG. 6 is a graph showing a mass spectrum of an epoxy resin obtained in Example 2.
Figure 7:
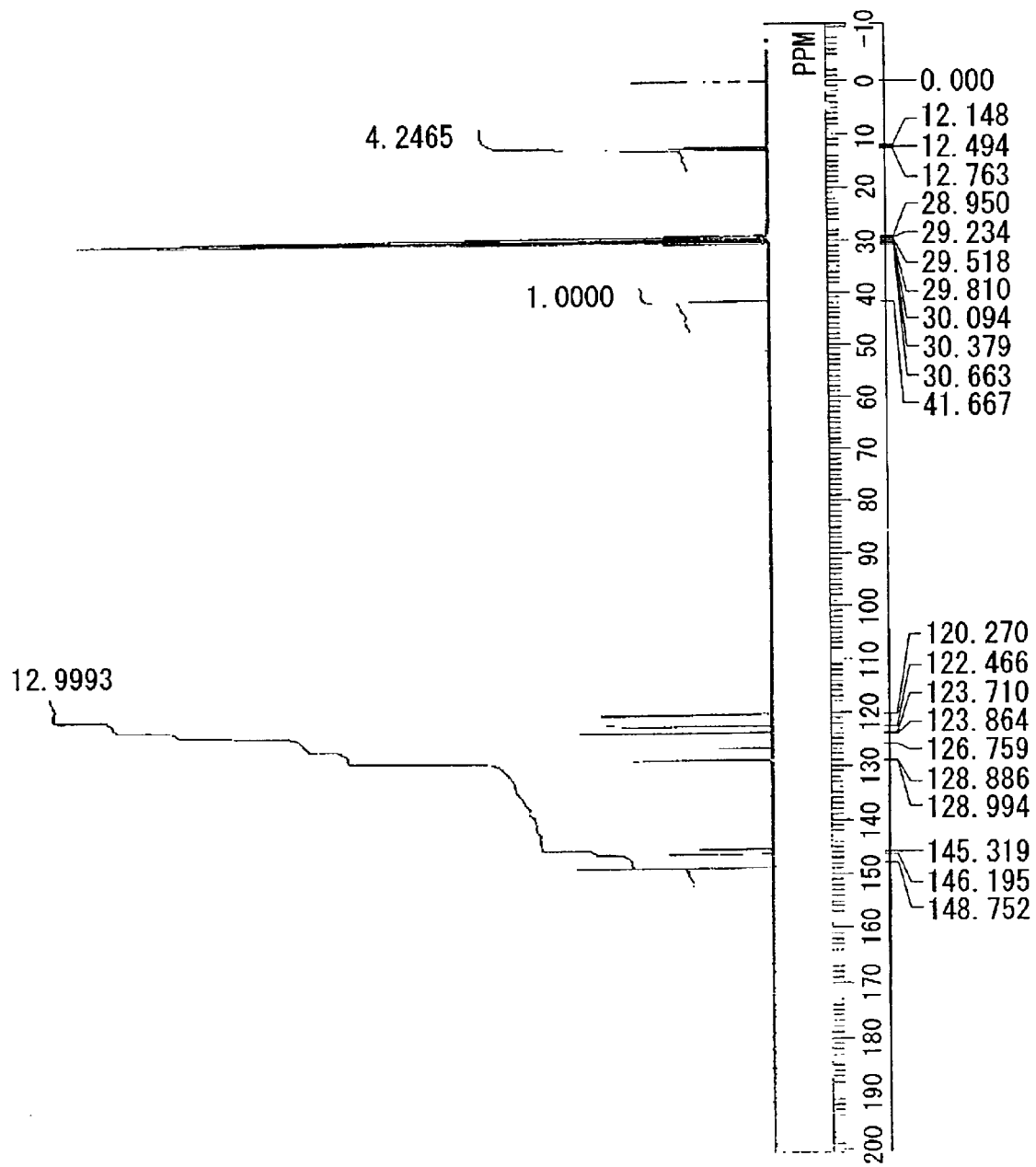
FIG. 7 is a graph showing a $^{13}$C NMR spectrum of a polyhydric hydroxy compound obtained in Example 3.
Figure 8:
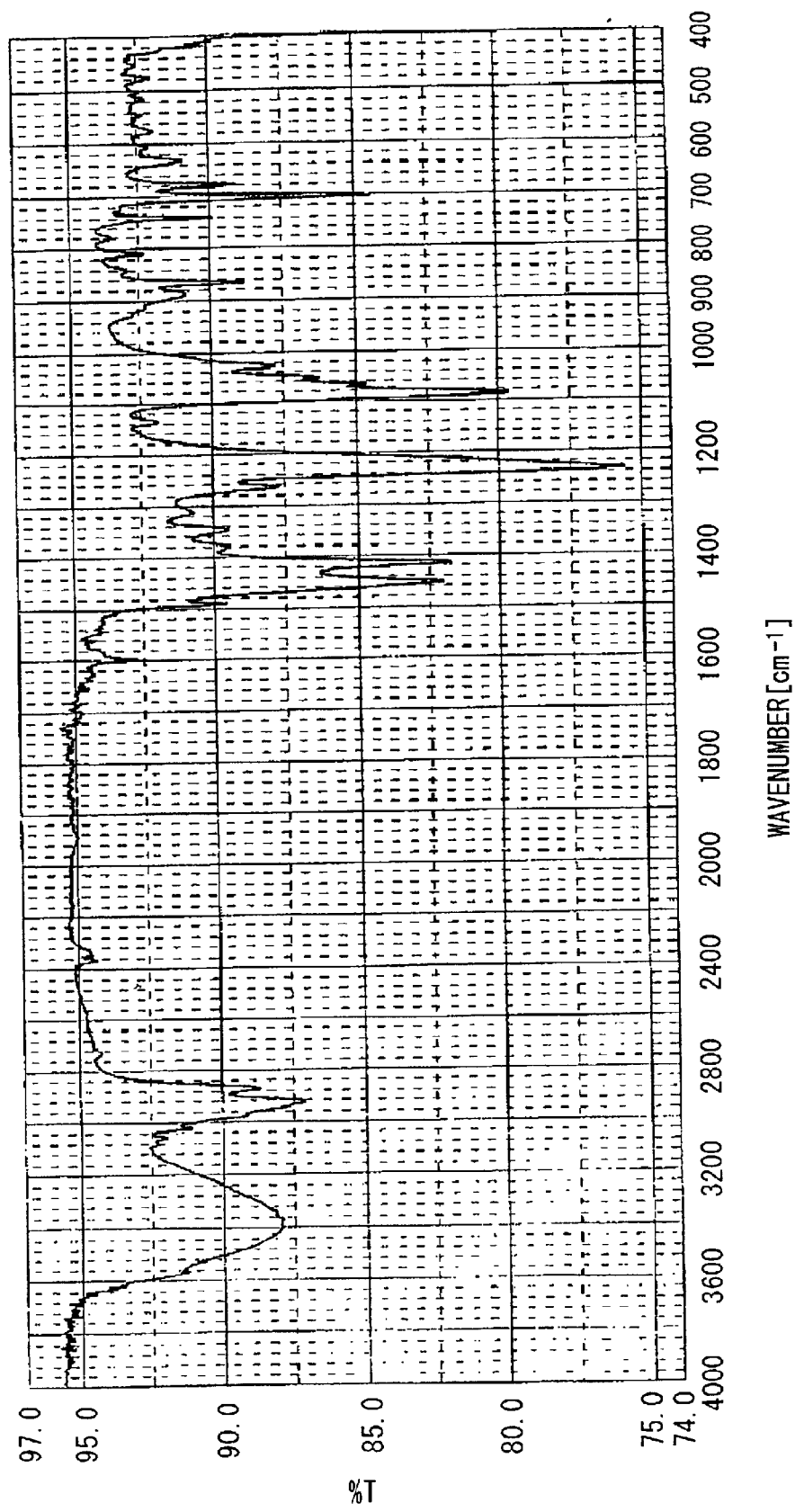
FIG. 8 is a graph showing an IR spectrum of a polyhydric hydroxy compound obtained in Example 3.
Figure 9:
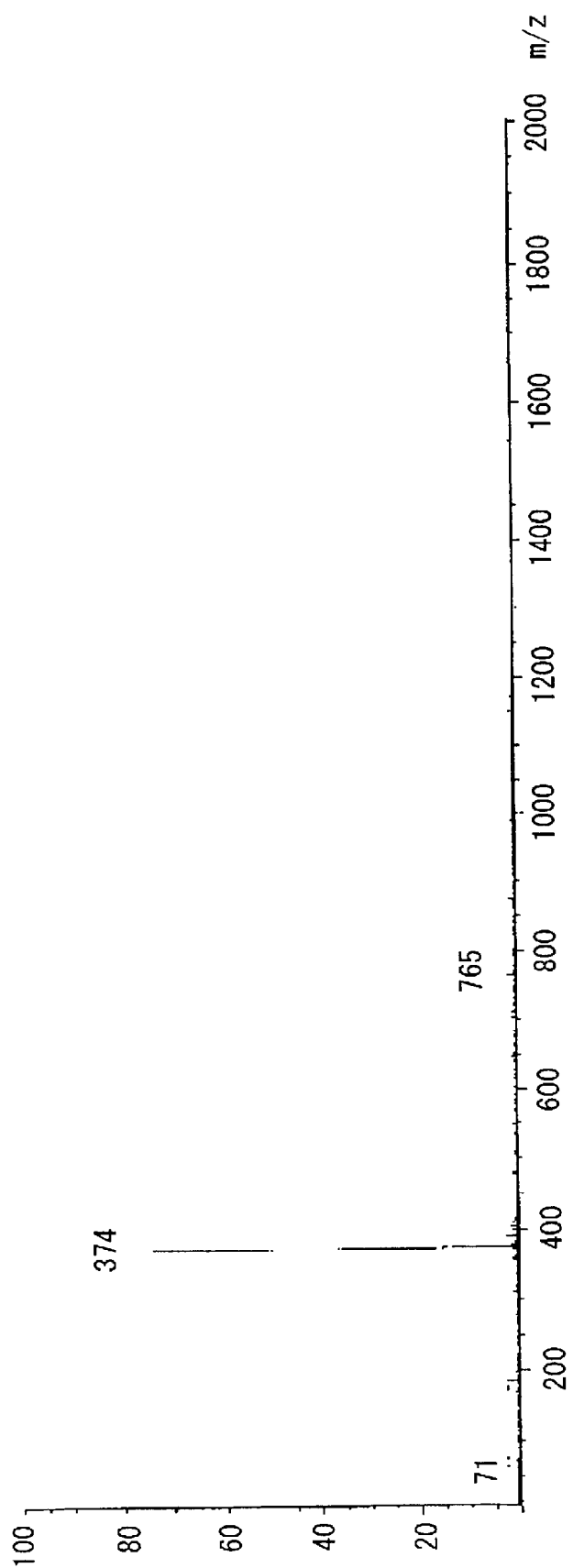
FIG. 9 is a graph showing a mass spectrum of a polyhydric hydroxy compound obtained in Example 3.
Figure 10:
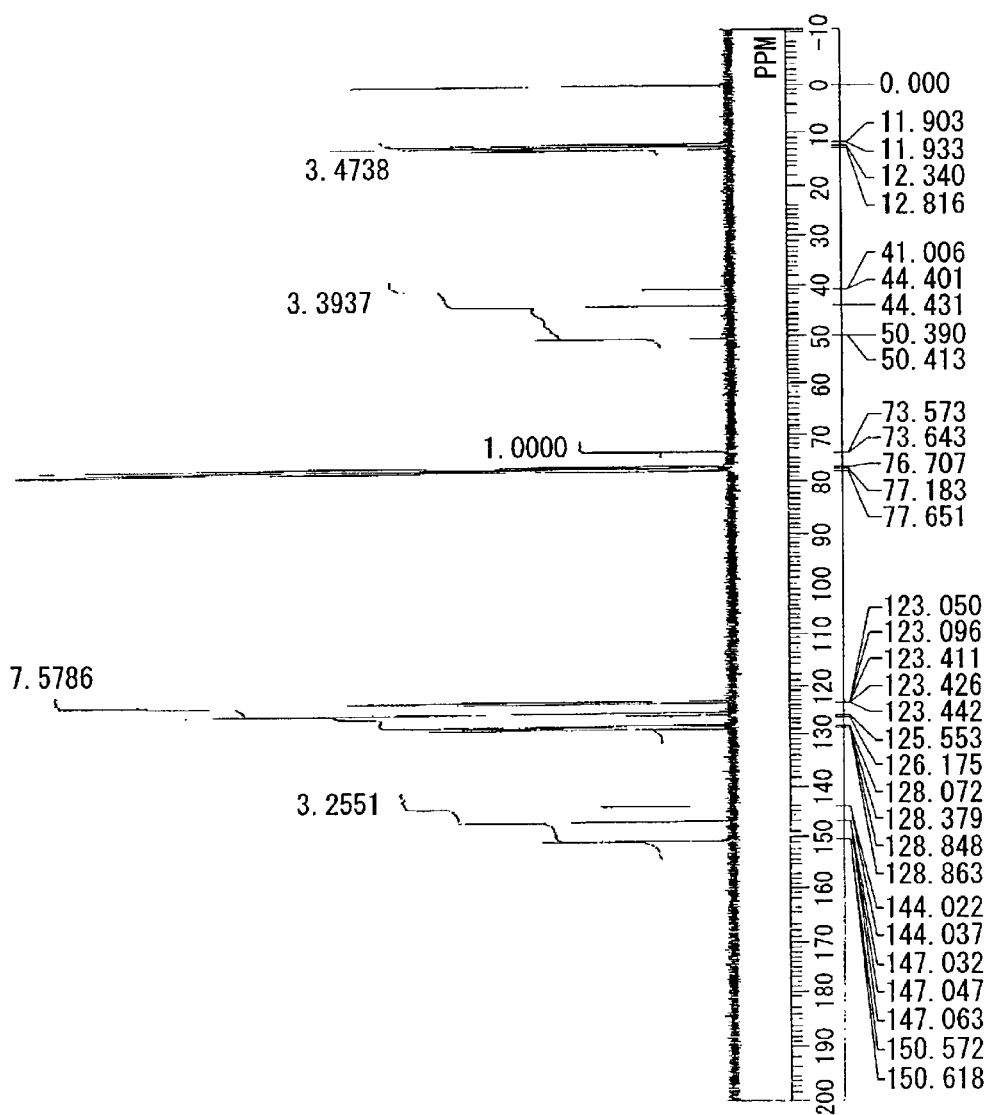
FIG. 10 is a graph showing a $^{13}$C NMR spectrum of an epoxy resin obtained in Example 4.
Figure 11:
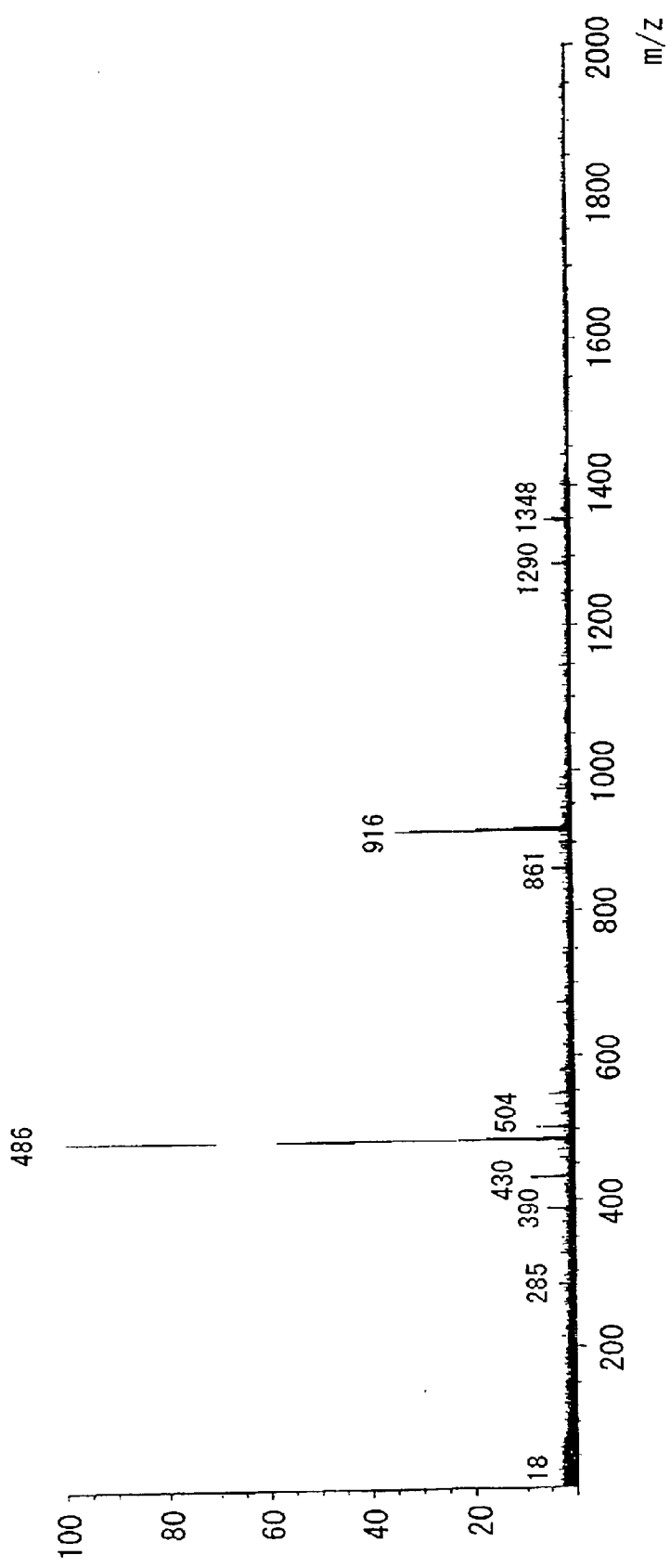
FIG. 11 is a graph showing an IR spectrum of an epoxy resin obtained in Example 4.
Figure 12:
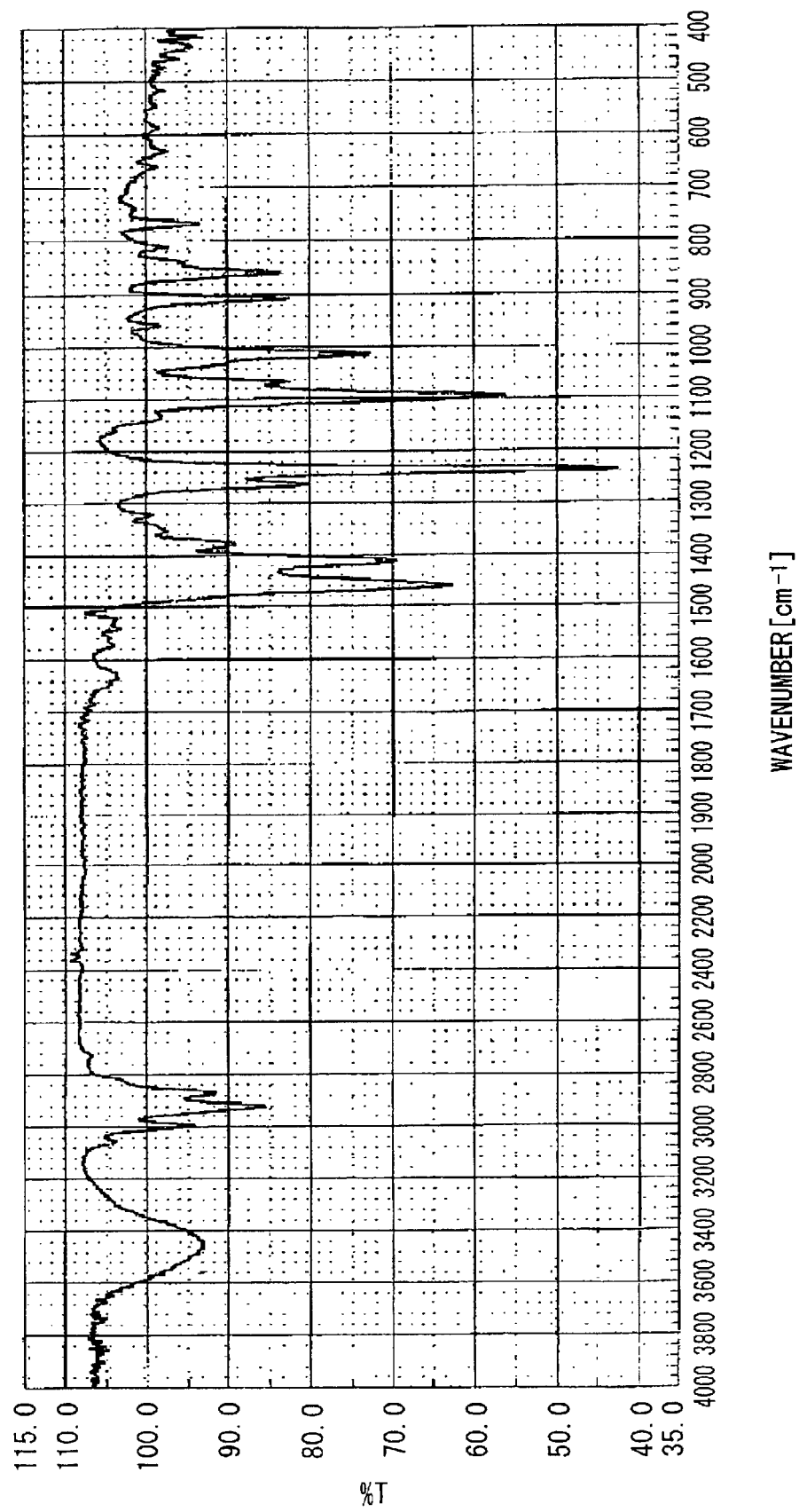
FIG. 12 is a graph showing a mass spectrum of an epoxy resin obtained in Example 4.

In the same manner as in Example 1, except that formalin was replaced by 64 g (0.6 mol) of benzaldehyde, 175 g (GPC purity: 99%) of the desired polyhydric hydroxy compound shown below was obtained. The structure was identified from a NMR spectrum ($^{13}C$) of FIG. 4, an IR spectrum (KBr) of FIG. 5 and a mass spectrum of FIG. 6.

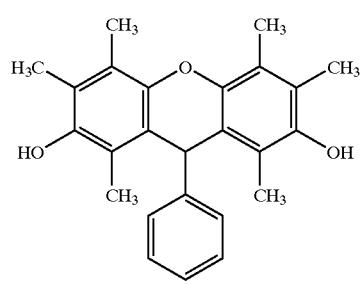

Example 4

In the same manner as in Example 2, except that the polyhydric phenol compound obtained in Example 1 was replaced by 187 g of the polyhydric phenol compound (hydroxyl group equivalent: 1.0 g/eq.) obtained in Example 3, 220 g of the desired epoxy resin (B) represented by the following structural formula was obtained. The epoxy equivalent of the resulting epoxy resin was 262 g/eq. The structure was identified from a NMR spectrum ($^{13}C$) of FIG. 4, an IR spectrum (KBr) of FIG. 5 and a mass spectrum of FIG. 6. It was confirmed from the GPC chart that the repeating unit number p of the following structural formula is 0.1.

Example 5

In the same manner as in Example 1, except that formalin was replaced by 197 g (1.2 mol) of biphenylaldehyde, 448 g (GPC purity: 99%) of the desired polyhydric phenol compound represented by the following structural formula was obtained. The hydroxyl group equivalent of this compound was 225 g/eq. (acetylation process) and the purity as measured by GPC was 99%.

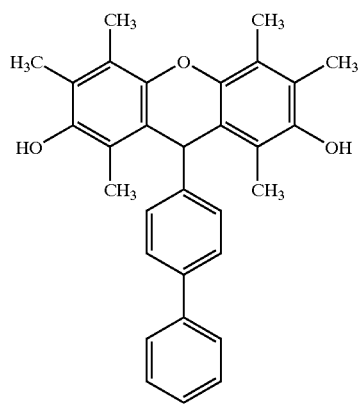

Example 6

In the same manner as in Example 2, except that the polyhydric phenol compound obtained in Example 1 was replaced by 225 g of the polyhydric phenol compound (hydroxyl group equivalent: 1.0 g/eq.) obtained in Example 5, 247 g of the desired epoxy resin (C) represented by the following structural formula was obtained. It was confirmed that the resulting epoxy resin is represented by the following structural formula because the epoxy equivalent of the resulting epoxy resin is 303 g/eq. and M+of the mass spectrum is 562. It was confirmed from GPC that the repeating unit number p of the following structural formula is 0.1.

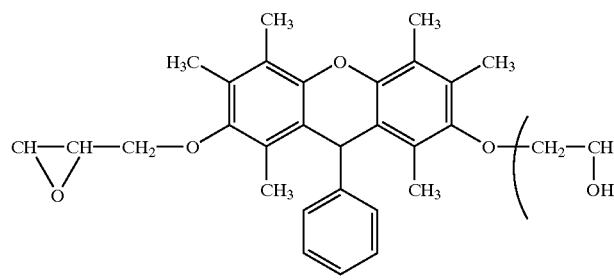

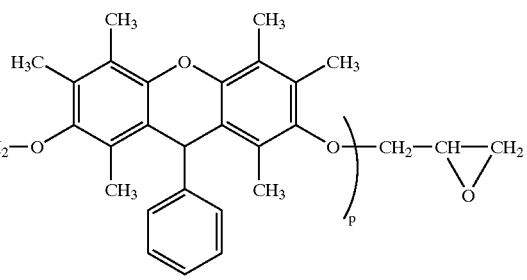

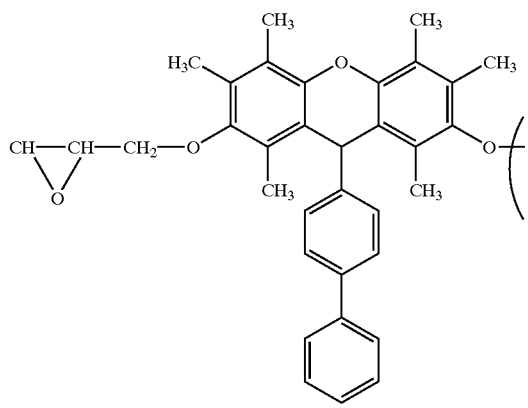
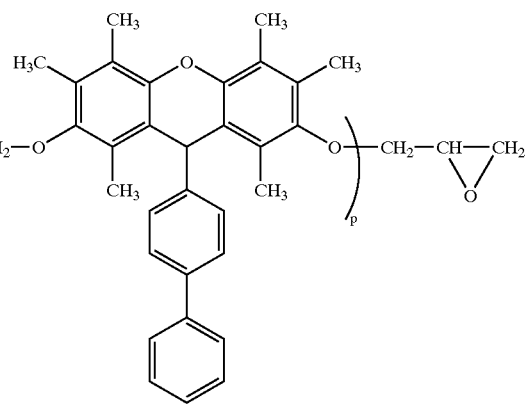

Example 7

In the same manner as in Example 1, except that 320 g (2.0 mol) of 2,7-dihydroxynaphthalene and formalin were replaced by 236 g (1.2 mol) of biphenylaldehyde, 276 g (GPC purity: 99%) of the desired polyhydric phenol compound represented by the following structural formula was obtained. The hydroxyl group equivalent of this compound was 157 g/eq. (acetylation process) and the purity as measured by GPC was 99%.

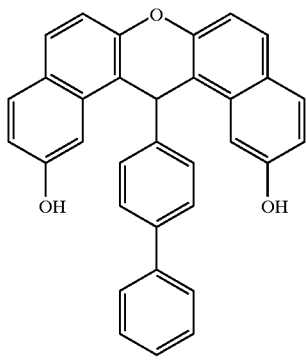

Example 8

In the same manner as in Example 2, except that the polyhydric phenol compound obtained in Example 1 was replaced by 157 g of the polyhydric phenol compound (hydroxyl group equivalent: 1.0 g/eq.) obtained in Example 7, 190 g of the desired epoxy resin (D) represented by the following structural formula was obtained. It was confirmed that the resulting epoxy resin is represented by the following structural formula because the epoxy equivalent of the resulting epoxy resin is 230 g/eq. and $M^+$ of the mass spectrum is 426. It was confirmed from GPC that the repeating unit number p of the following structural formula is 0.1.

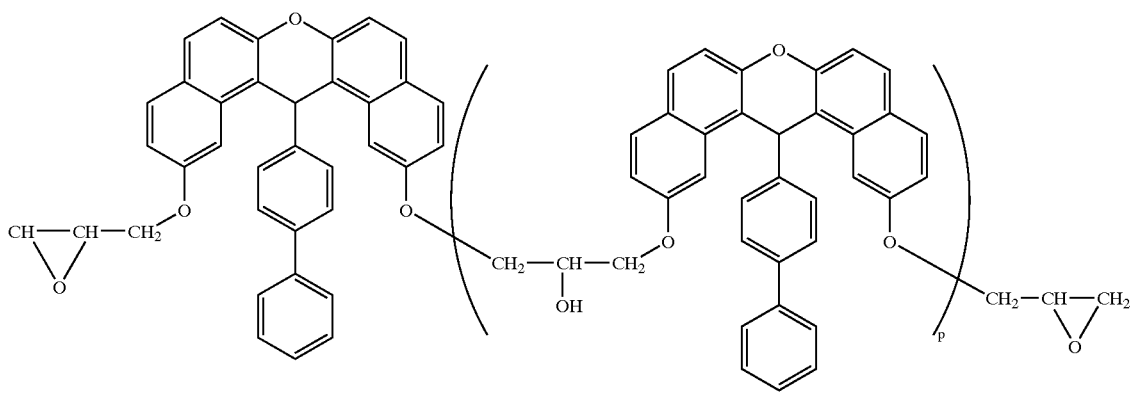

Example 9

In the same manner as in Example 1, except that formalin was replaced by 162 g (1.2 mol) of 4-methylbenzaldehyde, 388 g (GPC purity: 99%) of the desired polyhydric phenol compound represented by the following structural formula was obtained. The hydroxyl group equivalent of this compound was 194 g/eq. (acetylation process) and the purity as measured by GPC was 99%.

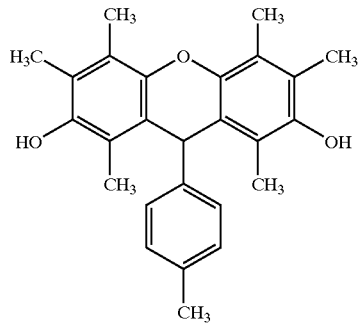

Example 11

In the same manner as in Example 1, except that formalin was replaced by 179 g (1.2 mol) of 3,4-methylbenzaldehyde, 399 g (GPC purity: 99%) of the desired polyhydric phenol compound represented by the following structural formula was obtained. The hydroxyl group equivalent of this compound was 201 g/eq. (acetylation process) and the purity as measured by GPC was 99%.

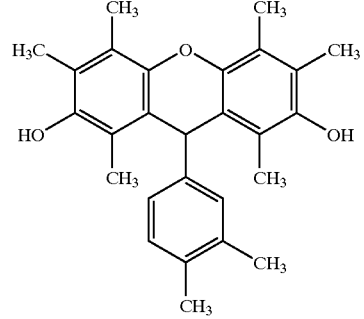

Example 10

In the same manner as in Example 2, except that the polyhydric phenol compound obtained in Example 1 was replaced by 194 g of the polyhydric phenol compound (hydroxyl group equivalent: 1.0 g/eq.) obtained in Example 9, 225 g of the desired epoxy resin (E) represented by the following structural formula was obtained. It was confirmed that the resulting epoxy resin is represented by the following structural formula because the epoxy equivalent of the resulting epoxy resin is 273 g/eq. and M+ of the mass spectrum is 500. It was confirmed from GPC that the repeating unit number p of the following structural formula is 0.1.

Example 12

In the same manner as in Example 2, except that the polyhydric phenol compound obtained in Example 1 was replaced by 201 g of the polyhydric phenol compound (hydroxyl group equivalent: 1.0 g/eq.) obtained in Example 11, 230 g of the desired epoxy resin (F) represented by the following structural formula was obtained. It was confirmed that the resulting epoxy resin is represented by the following structural formula because the epoxy equivalent of the resulting epoxy resin is 277 g/eq. and $M^+$ of the mass spectrum is 514. It was confirmed from GPC that the repeating unit number p of the following structural formula is 0.1.

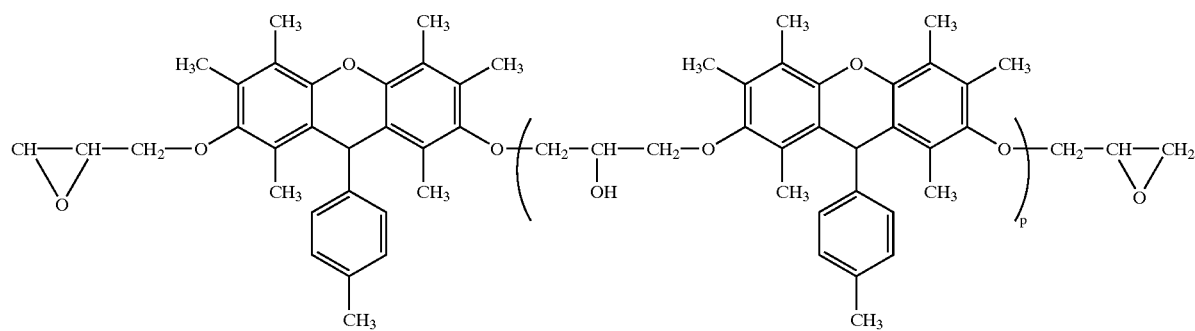

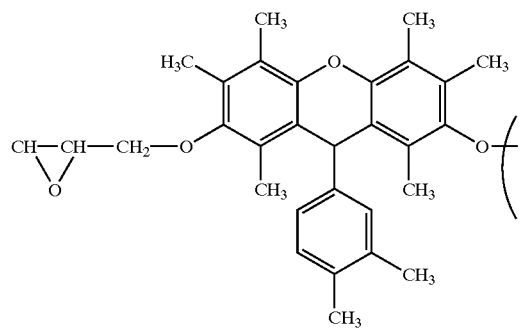

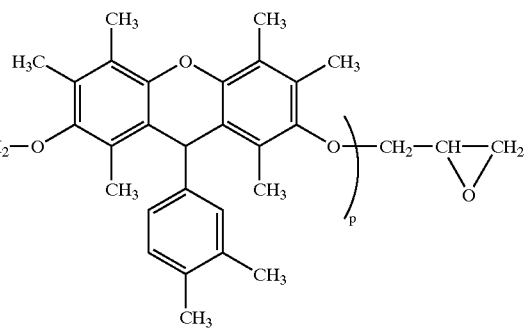

Example 13

In the same manner as in Example 1, except that formalin was replaced by 179 g (1.2 mol) of 2,3-dimethylbenzaldehyde, 398 g (GPC purity: 99%) of the desired polyhydric phenol compound represented by the following structural formula was obtained. The hydroxyl group equivalent of this compound was 201 g/eq. (acetylation process) and the purity as measured by GPC was 99%.

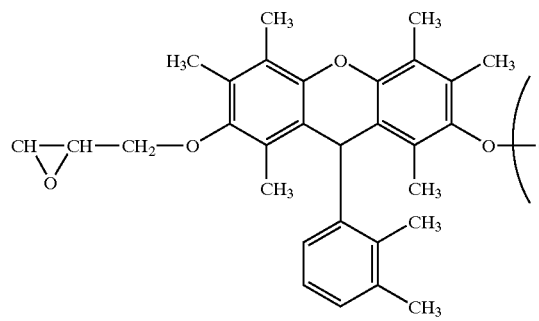

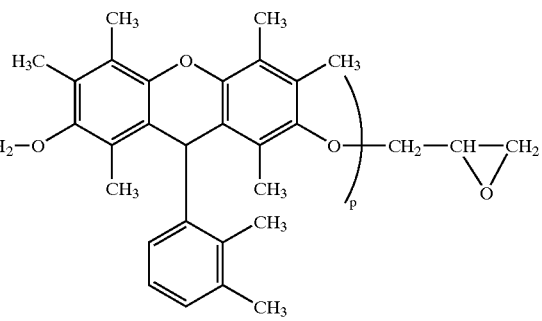

resulting epoxy resin is 276 g/eq. and $M^+$ of the mass spectrum is 514. It was confirmed from GPC that the repeating unit number p of the following structural formula is 0.1.

Example 15 to 17 and Comparative Example 1 to 2

The epoxy resins (A) to (C), a BPA type epoxy resin (EPICLON 850S: manufactured by DAINIPPON INK & CHEMICALS Co., Ltd.) and a cresol novolak type epoxy resin (EPICLON N-665-EXP-S: manufactured by DAINIPPON INK & CHEMICALS Co., Ltd.) as an epoxy resin for comparison, a phenolaralkyl resin (MILEX XLC-LL: manufactured by Mitsui Chemicals, Inc.) as a curing agent, triphenylphosphine (TPP) and a dicyclopentadiene-phenol polyadduct type epoxy resin (epoxy equivalent: 263 g/eq, softening point: 65° C., melt viscosity at 150° C.: 0.8 poise, manufactured by DAINIPPON INK & CHEMICALS Co., Ltd., EPICLON HP-7200)) as a curing accelerator, and a spherical silica as an inorganic filler were mixed in each formulation shown in Table 1 and each mixture was melt-kneaded at a temperature of 100° C. for 10 minutes using a twin roll to obtain the desired compositions. The composition shown in the table represents a mixing ratio by weight.

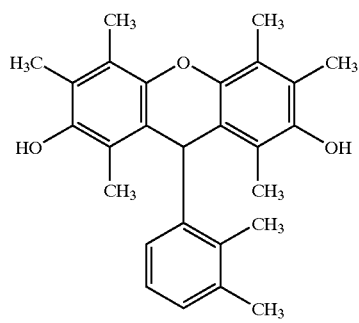

Example 14

In the same manner as in Example 1, except that the polyhydric phenol compound obtained in Example 1 was replaced by 201 g of the polyhydric phenol compound (hydroxyl group equivalent: 1.0 g/eq.) obtained in Example 13, 229 g of the desired epoxy resin (G) represented by the following structural formula was obtained. It was confirmed that the resulting epoxy resin is represented by the following structural formula because the epoxy equivalent of the Each composition was pressed at 180° C. for 10 minutes, cured at 180° C. for 5 hours, and then specimens having a thickness of 1.6 mm were made in accordance with the UL-94 test procedure. The results of the flame resistance test of the resulting specimens are shown in Table 1.

TABLE 1

|  | Examples | | | Comparative Examples | | |
|---|---|---|---|---|---|---|
|  | 15 | 16 | 17 | 1 | 2 | 3 |
| Epoxy resin (A) | 113 | | | | | |
| Epoxy resin (B) | | 120 | | | | |
| Epoxy resin (C) | | | 126 | | | |
| BPA type liquid epoxy resin | | | | 102 | | |
| Cresol novolak type epoxy resin | | | | | 107 | |
| Dicyclopentadiene-phenol polyadduct type epoxy resin | | | | | | 120 |
| Phenolaralkyl resin | 87 | 80 | 74 | 98 | 93 | 80 |
| Triphenylphosphine | 3 | 3 | 3 | 3 | 3 | 3 |
| Fumed silica | 800 | 800 | 800 | 800 | 800 | 800 |
| Glass transition temperature (DMA) | 175 | 172 | 170 | 112 | 157 | 139 |
| Moisture absorption ratio | 0.20 | 0.19 | 0.17 | 0.26 | 0.28 | 0.19 |
| Flame resistance test | V-0 | V-0 | V-0 | * | * | * |
| Flame resistance test Total combustion time of 5 samples | 28 | 15 | 7 | * | * | * |

*Specimens were combusted.

According to the present invention, it is made possible to exert an excellent flame-resistant effect while having properties required for semiconductor encapsulating materials and varnishes for circuit boards, for example, heat resistance, moisture resistance and dielectric performances in the epoxy resin composition. Furthermore, it is made possible to provide a novel epoxy resin having these performances suited for use as the epoxy resin composition, and a phenol compound suited for use as an intermediate of the novel epoxy resin.

The use of the epoxy resin composition for a ball grid array type semiconductor chip makes it possible to prevent warp, which has hitherto been considered to be a problem, and to obtain a package having excellent solder cracking resistance when it is mounted. The use of the epoxy resin composition for a printed circuit board makes it possible to obtain a multi-layer board having high glass transition temperature and excellent dimensional stability. Since excellent flame resistance can be imparted to the cured article without containing a halogen compound, the epoxy resin is markedly useful as epoxy resin materials in the field of electronic materials, for example, semiconductor encapsulating materials and printed circuit boards.

What is claimed is:

1. An epoxy resin composition comprising an epoxy resin and a curing agent, wherein the epoxy resin has an aromatic polycyclic structure having a methyl group in which two aromatic hydrocarbons are bonded through carbon atoms or oxygen atoms in two adjacent substitution positions on an aromatic ring in the aromatic hydrocarbon, and also has glycidyloxy groups as a substituent on the aromatic polycyclic structure as well.

2. An epoxy resin composition comprising an epoxy resin and a curing agent, wherein the epoxy resin has a chemical structure represented by the following general formula (2):

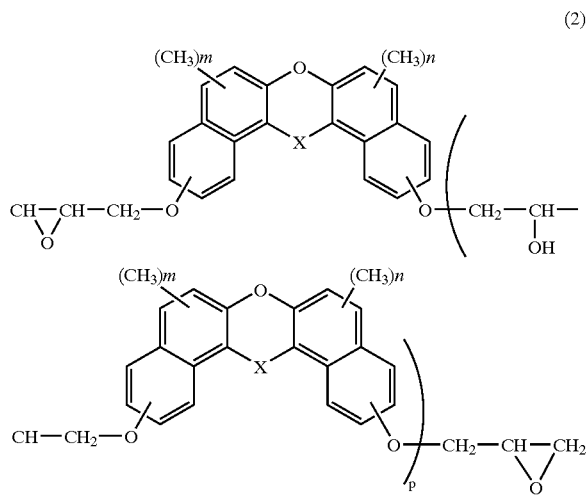

(2)

in the general formula (2), X represents oxygen atom, a methylene group, a methylene group substituted with an alkyl group having 1 to 4 carbon atoms, a methylene group substituted with a phenyl group, a methylene group substituted with a naphthyl group, a methylene group substituted with a biphenyl group, a methylene group substituted with a 9-fluorenyl group, or a methylene group in which an alkyl group is further aromatic nucleus-substituted on the phenyl group, the naphthyl group or the biphenyl group, n and m represents an integer of 0 to 5, and p represents an average repeated unit number of 0 to 10.

3. A composition according to claim 1, wherein the epoxy resin has an epoxy equivalent of 240 to 330 g/eq.

4. A composition according to claim 1, wherein the number of carbon atoms constituting the aromatic polycyclic structure portion accounts for 20% or more of the number of aromatic carbon atoms in the epoxy resin.

5. A composition according to claim 1, which further contains 65 to 95% by weight of an inorganic filler, in addition to the epoxy resin and the curing agent.

6. A novel epoxy resin represented by the general formula (1):

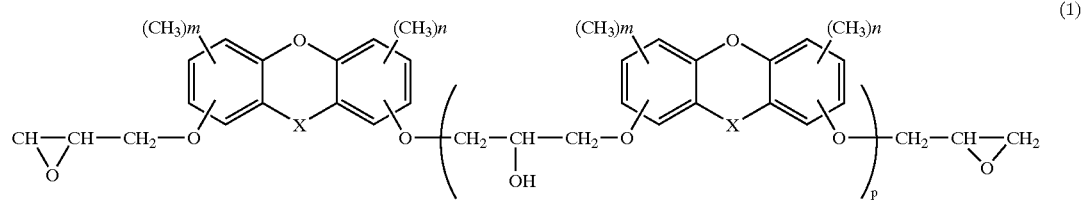

(1)

in the general formula (1), X represents oxygen atom, a methylene group, a methylene group substituted with an alkyl group having 1 to 4 carbon atoms, a methylene group substituted with a phenyl group, a methylene group substituted with a naphthyl group, a methylene group substituted with a biphenyl group, a methylene group substituted with a 9-fluorenyl group, or a methylene group in which an alkyl group is further aromatic nucleus-substituted on the phenyl group, the naphthyl group or the biphenyl group, n and m represent an integer of 1 to 3, and p represents an average repeated unit number of 0 to 10.

7. A novel epoxy resin represented by the general formula (2):

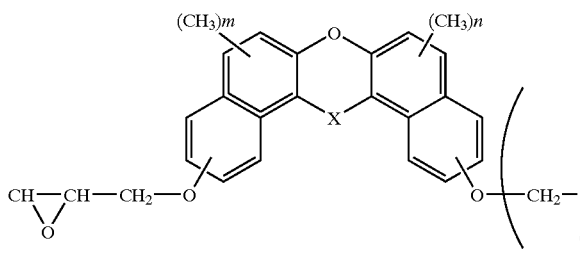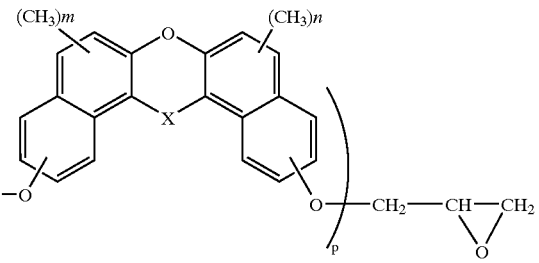

(2)

in the general formula (2), X represents oxygen atom, a methylene group, a methylene group substituted with an alkyl group having 1 to 4 carbon atoms, a methylene group substituted with a phenyl group, a methylene group substituted with a naphthyl group, a methylene group substituted with a biphenyl group, a methylene group substituted with a 9-fluorenyl group, or a methylene group in which an alkyl group is further aromatic nucleus-substituted on the phenyl group, the naphthyl group or the biphenyl group, n and m represents an integer of 0 to 5, and p represents an average repeated unit number of 0 to 10.

8. A novel phenol compound represented by the general formula (4):

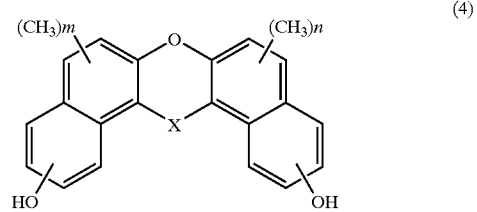

(4)

in the general formula (4), X represents oxygen atom, a methylene group, a methylene group substituted with an alkyl group, a methylene group substituted with a phenyl group, a methylene group substituted with a naphthyl group, a methylene group substituted with a biphenyl group, a methylene group substituted with a 9-fluorenyl group, or a methylene group in which an alkyl group is further aromatic nucleus-substituted on the phenyl group, the naphthyl group or the biphenyl group, and n and m represent an integer of 0 to 5.

9. A process for preparing a polyhydric hydroxy compound, which comprises reacting a compound having two hydroxyl groups on the benzene ring, one of the hydroxyl groups having a hydrogen atom at the ortho-position and a substituent at all of other substitution positions, with a carbonyl group-containing compound in the presence of an acid catalyst.

10. A process according to claim 9, wherein 1 mol of the compound having two hydroxyl groups on the benzene ring, one of the hydroxyl groups having a hydrogen atom at the ortho-position and a substituent at all of the other substitution positions, is reacted with 0.1 to 3.0 mol of the carbonyl group-containing compound under the temperature condition of 50 to 200° C.

11. A cured article obtained by thermally curing the composition of any one of claims 1 to 5.

12. A composition according to claim 2, wherein the epoxy resin has an epoxy equivalent of 240 to 330 g/eq.

13. A composition according to claim 2, wherein the number of carbon atoms constituting the aromatic polycyclic structure portion accounts for 20% or more of the number of aromatic carbon atoms in the epoxy resin.

14. A composition according to claim 2, which further contains 65 to 95% by weight of an inorganic filler, in addition to the epoxy resin and the curing agent.

15. A process for preparing a polyhydric hydroxyl compound, which comprises reacting a dihydroxynaphthalene having hydrogen atoms at the position adjacent to hydroxyl groups with a carbonyl group-containing compound in the presence of an acid catalyst.

16. A process according to claim 15, wherein 1 mol of the dihydroxynaphthalene having hydrogen atoms at the position adjacent to hydroxyl groups, is reacted with 0.1 to 3.0 mol of the carbonyl group-containing compound under the temperature condition of 50 to 200° C.

17. A process for preparing an epoxy resin, which comprises:

Step 1: reacting a dihydroxynaphthalene having hydrogen atoms at the position adjacent to hydroxyl group with a carbonyl group-containing compound in the presence of an acid catalyst, and Step 2: reacting the obtained compound with an epihalohydrin.

18. A process according to claim 17, wherein 1 mol of the dihydroxynaphthalene having hydrogen atoms at the position adjacent to hydroxyl groups, is reacted with 0.1 to 3.0 mol of the carbonyl group-containing compound under the temperature condition of 50 to 200° C. in the step 1.

* * * * *